United States Patent
Waas et al.

(10) Patent No.: US 10,258,642 B2
(45) Date of Patent: Apr. 16, 2019

(54) DEXTRAN SULFATE FOR USE IN MOBILIZATION OF CELLS

(71) Applicant: TX MEDIC AB, Viken (SE)

(72) Inventors: Anders Waas, Göteborg (SE); Ida Duprez, Täby (SE)

(73) Assignee: TX MEDIC AB, Viken (SE)

( * ) Notice: Subject to any disclaimer, the term of this patent is extended or adjusted under 35 U.S.C. 154(b) by 0 days.

(21) Appl. No.: 14/890,636

(22) PCT Filed: May 12, 2014

(86) PCT No.: PCT/SE2014/050576
§ 371 (c)(1),
(2) Date: Nov. 12, 2015

(87) PCT Pub. No.: WO2014/185851
PCT Pub. Date: Nov. 20, 2014

(65) Prior Publication Data
US 2016/0120897 A1 May 5, 2016

(30) Foreign Application Priority Data

May 13, 2013 (SE) ...................... 1350584

(51) Int. Cl.
*A61K 31/737* (2006.01)
*A61K 38/19* (2006.01)
*A61K 38/18* (2006.01)
*A61K 9/00* (2006.01)

(52) U.S. Cl.
CPC .......... *A61K 31/737* (2013.01); *A61K 9/0019* (2013.01); *A61K 38/1833* (2013.01); *A61K 38/193* (2013.01)

(58) Field of Classification Search
CPC ............................ A61K 31/737; A61K 38/193
See application file for complete search history.

(56) References Cited

U.S. PATENT DOCUMENTS 3,498,972 A 3/1970 Nagasawa
2006/0111319 A1 5/2006 Nilsson et al.

FOREIGN PATENT DOCUMENTS

| CN | 1589904 A | 3/2005 |
|---|---|---|
| CN | 1717240 A | 1/2006 |
| JP | 47-30167 | 8/1972 |

OTHER PUBLICATIONS

Raghavachar et al., Int J Cell Cloning. Sep. 1983;1(4):191-205.*
Rosu-Myles J Cell Sci. 2005;118:4343-4352.*
CN15899904 English translation, 2014.*
De Jong et al., Blood. Dec. 1, 1995;86(11):4076-4085.*
Di Giacomo et al., Haematologica. Apr. 2012;97(4):491-499.*
Sasaki et al., nature 216:1013-1016 (Year: 1967).*
Partial translation of Yang et al., Journal of shantou University Medical College 17:15-17 (Year: 2004).*
Broxmeyer et al., Dominant Myelopoietic Effector Functions Mediated by Chemokine Receptor CCR1, The Journal of Experimental Medicine, 189(12):1987-1992 (Jun. 21, 1999).
Fiorante et al., Low molecular weight dextran sulfate prevents complement activiation and delays hyperacute rejection in pig-to-human xenotransplantation models, Xenotransplantation, 8:24-35 (2001).
Han et al., Effect of combination of DS and G-CSF on mobilization of peripheral hematopoietic progenitors in mice, Journal of Experimental Hematology, 6(1):29-31 (1998), w/English abstract on p. 31.
Hayakawa et al., Dextran Sulfate and Stromal Cell Derived Factor-1 Promote CXCR4 Expression and Improve Bone Marrow Homing Efficiency of Infused Hematopoietic Stem Cells, J Nippon Med Sch 76(4):198-208 (2009).
Ma et al., Role of Low molecular dextran sulfate in mobilization of stem cell in beagle, Bulletin of the Academy of Military Medical Sciences, 120(1)19-22 (1996), with English abstract on p. 19.
Ma et al., Experiemental Study and Normal Individual Trial of Hemopoietic Stem Cell Mobilizer DS, The Internal Journal of Cell Cloning, Supplement: Peripheral Blood Stem Cell Autografts, 10(S1): 41-43 (1992).
Schmidt et al., Low Molecular Weight Dextran Sulfate Is Well Tolerated in Humans and Increases Endogenous Expression of Islet Protective Hepatocyte Growth Factor, Transplantation 86(11):1523-1529 (2008).
Sweeney et al., Mobilization of stem/progenitor cells by sulfated polysaccharides does not require selectin presence, PNAS, 97(12):6544-6549 (2000).
Sweeney et al., Sulfated polysaccharides increase plasma levels of SDF-1 in monkeys and mice: involvement in mobilization of stem/progenitor cells, Blood, 99(1):44-51 (2002).
Dextrans, Sigma-Aldrich Co. LLC., Extract from www.sigmaaldrich.com (2013).
Min Yang et al., Study on Bone Marrow Stem Cells Induced in Myocardium Micro-condition in vivo, Journal of Shantou University Medical College, vol. 17, Issue 1, pp. 15-17 (Dec. 31, 2004) with English Abstract.
Puen Ma et al., The role of dextran sulfate with low molecular weight in mobilization of the stem cell in Beagle, Chinese Journal of Hematology, vol. 17, Issue 5, pp. 251-253 (May 31, 1996), with English Abstract.
Official Action and Search Report dated Nov. 15, 2017 from corresponding Chinese Application No. 2014800388335, and English Translation of Search Report.
Sasake et al. Mobilization of Lymphocytes from Lymph Nodes and Spleen by Polysaccharide Polysulphate, Nature, vol. 216 p. 1013-1016 (Dec. 9, 1967).
Official Action dated Jan. 9, 2018 from corresponding Japanese Application No. 2016-513900, and English Translation.

* cited by examiner

*Primary Examiner* — Daniel C Gamett
(74) *Attorney, Agent, or Firm* — Porter Wright Morris & Arthur LLP

(57) ABSTRACT

Dextran sulfate in a range of 3500 and 9500 Da is employed to mobilize cells, such as stem and/or progenitor cells and certain white blood cells, in particular lymphocytes, into the peripheral blood of a subject. Dextran sulfate has a very fast cell mobilizing effect that implies that any cell harvest can be started almost immediately following dextran sulfate administration.

17 Claims, 15 Drawing Sheets

DEXTRAN SULFATE FOR USE IN MOBILIZATION OF CELLS

TECHNICAL FIELD

The embodiments generally relate to mobilization of cells into the blood stream of a subject.

BACKGROUND

Stem cells and progenitor cells are immature cells with capacity to divide and develop to form any cell type of the mature system. Hematopoietic stem cells (HSC) are able to produce the cells of the immune system and bone marrow. HSC transplantation (HSCT) is used to restore normal hematopoiesis in a patient to treat various diseases after chemotherapy or radiation. During the last couple of decades, HSCT has become a clinical routine treatment for a variety of conditions including multiple myeloma (MM), non-Hodgkin's lymphoma (NHL) and conditions requiring allograft transplantation. Despite the apparent improvements during recent years, the procedure is still associated with a comparably high rate of morbidity and mortality due to complications and relapse of the underlying disease. There is also a continuous need for improving stem cell sources, cell harvesting procedures, conditioning regimens and immunosuppressive treatment. There are two major kinds of HSCT, either allogenic—with stem cells originating from a compatible healthy donor, or autologous—when stem cells are collected from and later given back to the same patient following high dose chemotherapy/radiotherapy conditioning therapy. In allogenic and particularly autologous HSCT, peripheral blood has today almost completely replaced bone marrow as the source for stem cells. Peripheral blood as cell source is preferred since it involves a less invasive procedure for the donor and engraftment of transplanted cells is faster as compared to using bone marrow as the cell source.

Despite the apparent improvements during recent years, the procedure is still associated with a comparably high rate of morbidity and mortality due to transplantation-related complications (mainly allogenic) and relapse of the underlying disease (mainly autologous). Hence, there is a continuous need for improving stem cell sources, cell harvesting protocols, conditioning regimens and immunosuppressive treatment.

Today, stem cells are mobilized to peripheral blood by treatment of the donor with granulocyte-colony stimulation factor (G-CSF) and the cells are harvested by apheresis for subsequent transplantation. After infusion in the recipient's bloodstream, the healthy hematopoietic cells migrate to the bone marrow where they can differentiate to yield mature blood cells and restore hematopoiesis. Recently plerixafor (MOZOBIL™, AMD3100, 1,1'-[1,4-phenylenebis (methylene)]-bis-1,4,8,11-tetraazacyclotetradecane) has been approved in combination with G-CSF to increase mobilization of progenitor cells in MM and NHL patients.

A significant limitation with the combinatory treatment with G-CSF and plerixafor is the slowness in stem cell mobilization. Although, experimental data in mice indicates a peak in mobilized stem cells following 1 hour after plerixafor administration (Broxmeyer 2005), the corresponding peak in humans starts first around 9 hours following plerixafor administration (Mozobil™ Product Monograph). Thereby, the harvest of mobilized stem cells is delayed until about 11 hours after the plerixafor administration, implying long hospitalization times (Mozobil™ Product Monograph). It is therefore the practice that plerixafor needs to be administered the day before the actual cell harvest.

Sweeney 2000 and Sweeney 2002 investigated the effects of sulfated polysaccharides, including 10 kDa dextran sulfate, in mobilization of stem/progenitor cells in mice and monkeys. In mice and monkeys dextran sulfate resulted in mobilization of colony forming cells (CFCs) following 3 hours and 6 hours, respectively, from dextran sulfate administration. The results presented in Sweeney 2000 and Sweeney 2002 therefore seem to indicate that dextran sulfate is about three times slower as compared to plerixafor in terms of mobilizing stem/progenitor cells.

SUMMARY

It is a general objective to provide an efficient mobilization of target cells into the blood stream of a subject.

It is another general objective to provide a high level of mobilized target cells in the blood stream of a subject.

These and other objectives are met by embodiments disclosed herein.

An aspect of the embodiments relates to dextran sulfate having an average molecular weight in a range of 3500 and 9500 Da, or a pharmaceutically acceptable derivate thereof, for use in mobilizing progenitor and/or stem cells into the peripheral blood of a subject. A related aspect of the embodiments defines the use of dextran sulfate having an average molecular weight in a range of 3500 and 9500 Da, or a pharmaceutically acceptable derivate thereof, for the manufacture of a medicament for mobilizing progenitor and/or stem cells into the peripheral blood of a subject. Another related aspect of the embodiments defines a method of mobilizing progenitor and/or stem cells into the peripheral blood of a subject. The method comprises administering an effective amount of dextran sulfate having an average molecular weight in a range of 3500 and 9500 Da, or a pharmaceutically acceptable derivate thereof, to the subject.

Another aspect of the embodiments relates to dextran sulfate having an average molecular weight in a range of 3500 and 9500 Da, or a pharmaceutically acceptable derivate thereof, for use in mobilizing target white blood cells, in particular lymphocytes, into the blood stream of a subject. A related aspect of the embodiments defines the use of dextran sulfate having an average molecular weight in a range of 3500 and 9500 Da, or a pharmaceutically acceptable derivate thereof, for the manufacture of a medicament for mobilizing target white blood cells, in particular lymphocytes, into the blood stream of a subject. Another related aspect of the embodiments defines a method of mobilizing target white blood cells, in particular lymphocytes, into the blood stream of a subject. The method comprises administering an effective amount of dextran sulfate having an average molecular weight in a range of 3500 and 9500 Da, or a pharmaceutically acceptable derivate thereof, to the subject.

A further aspect of the embodiments relates to a cell mobilizing composition comprising dextran sulfate having an average molecular weight in a range of 3500 and 9500 Da, or a pharmaceutically acceptable derivative thereof, and granulocyte-colony stimulation factor (G-CSF). Other related aspects of the embodiments defines a cell mobilizing composition comprising dextran sulfate having an average molecular with in a range of 3500 and 9500 Da, or a pharmaceutically acceptable derivative thereof, and G-CSF for use in mobilizing progenitor and/or stem cells into the peripheral blood of a subject and/or for use in mobilizing target white blood cells, in particular lymphocytes, into the blood stream of a subject. Further related aspects of the embodiments defines the use of a cell mobilizing composition comprising dextran sulfate having an average molecular with in a range of 3500 and 9500 Da, or a pharmaceutically acceptable derivative thereof, and G-CSF for the manufacture of a medicament for mobilizing progenitor and/or stem cells into the peripheral blood of a subject and/or for mobilizing target white blood cells, in particular lymphocytes, into the blood stream of a subject. Yet other related aspects of the embodiments defines a method of mobilizing progenitor and/or stem cells into the peripheral blood of a subject or mobilizing target white blood cells, in particular lymphocytes, into the blood stream of a subject. The method comprises administering an effective amount, to the subject, of a cell mobilizing composition comprising dextran sulfate having an average molecular with in a range of 3500 and 9500 Da, or a pharmaceutically acceptable derivative thereof, and G-CSF.

In an embodiment, the pharmaceutically acceptable derivative is preferably a pharmaceutically acceptable salt of dextran sulfate.

The inventors have found that dextran sulfate of a narrow range with regard to the average molecular weight achieves a significant improvement in cell mobilization as compared to dextran sulfate molecules having smaller or larger average molecular weights.

Dextran sulfate molecules having an average molecular weight below the range of the present embodiments do not have any significant effect in terms of mobilizing progenitor and/or stem cells or white blood cells. Dextran sulfate molecules having an average molecular weight above the range of the present embodiments do not seem to have any additive effect and no synergistic effect when used together with other cell mobilizing compounds, such as G-CSF, and seem to have slower mobilization effect as compared to the present embodiments.

The present embodiments provide an efficient cell mobilization with an unexpected mobilizing profile triggering cell mobilization almost immediately following dextran sulfate administration with a peak in mobilized cells starting already within 7.5-30 minutes after dextran sulfate administration in mice and within 30-120 minutes in humans. The dextran sulfate molecules of the embodiments can additionally be synergistically combined with other cell mobilizing compounds to even further increase the number of mobilized cells.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

The present embodiments generally relate to cell mobilization in animals, preferably mammals, and in particular humans. In particular, the embodiments relate to mobilization of stem and/or progenitor cells and/or certain white blood cells that can be used, for instance, in cell transplantation, including hematopoietic stem cell transplantation (HSCT).

The embodiments are based on unexpected characteristics of dextran sulfate relating to mobilization of cells in a subject, preferably a mammalian subject and more preferably human subject.

An aspect of the embodiments therefore relates to dextran sulfate having an average molecular weight in a range of 3500 and 9500 Da, or a pharmaceutically acceptable derivate thereof, for use in mobilizing progenitor and/or stem cells, typically from the bone marrow (BM), into the peripheral blood (PB) of a subject, preferably a mammalian subject, and more preferably a human subject.

In the peripheral blood, the stem and/or progenitor cells are available for harvest and can thereby be used in cell transplantation, including HSCT. Alternatively, the mobilization of the stem and/or progenitor cells into the peripheral blood can achieve advantageous effects without being harvested from the subject, for instance circulated in vivo for tissue or organ repair, such as myocardial repair.

An embodiment of this aspect therefore relates to a method of mobilizing progenitor and/or stem cells, preferably from the bone marrow, into the peripheral blood of a subject, preferably a human subject. The method comprises administering an effective amount of dextran sulfate having an average molecular weight in a range of 3500 and 9500 Da, or a pharmaceutically acceptable derivate thereof, to the subject. Another embodiment of this aspect relates to the use of dextran sulfate having an average molecular weight in a range of 3500 and 9500 Da, or a pharmaceutically acceptable derivative thereof, for the manufacture of a medicament for mobilizing progenitor and/or stem cells, preferably from the bone marrow, into the peripheral blood of a subject, preferably a human subject.

The expression "progenitor cells" refers herein to certain cells that can form differentiated hematopoietic or myeloid cells in response to stimuli. Progenitor cells in a sample can be identified by their ability to form colony forming units (CFUs) of various types. Such CFU types include CFU-granulocyte, macrophage (CFU-GM), CFU-granulocyte, erythrocyte, monocyte, megakarocyte (CFU-GEMM), burst forming unit-erythrocyte (BFU-E) among others. "Stem cells" are less differentiated forms of progenitor cells and typically, though not always, express the cell surface glycoprotein CD34 in humans.

Figure 10:
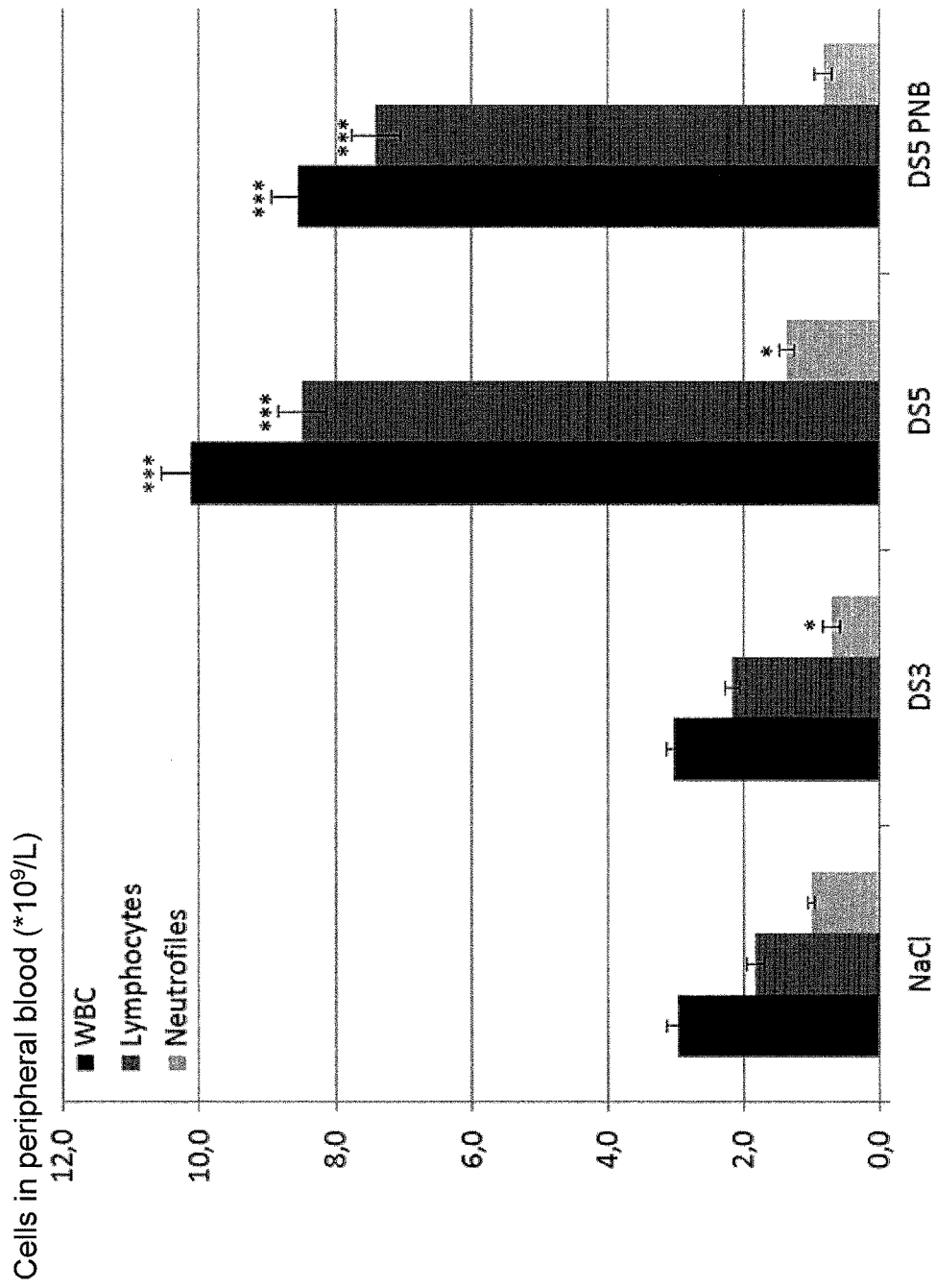
FIG. 10 illustrates the effects of dextran sulfate on white blood cells in peripheral blood. The animals were treated with a single i.v. injection of dextran sulfate of different average molecular weights (DS3 or DS5) in doses of 50 mg/kg. Buffered saline (NaCl) was used as vehicle control. Some animals were sedated using penta-sodium barbital (PNB) instead of isoflurane to compare the effect of different methods of anesthesia. Error bars show SEM. Student t-test was used to evaluate statistically significant differences compared to control group (*$p<0.05$, $p<0.01$, *$p<0.001$).
Figure 11:
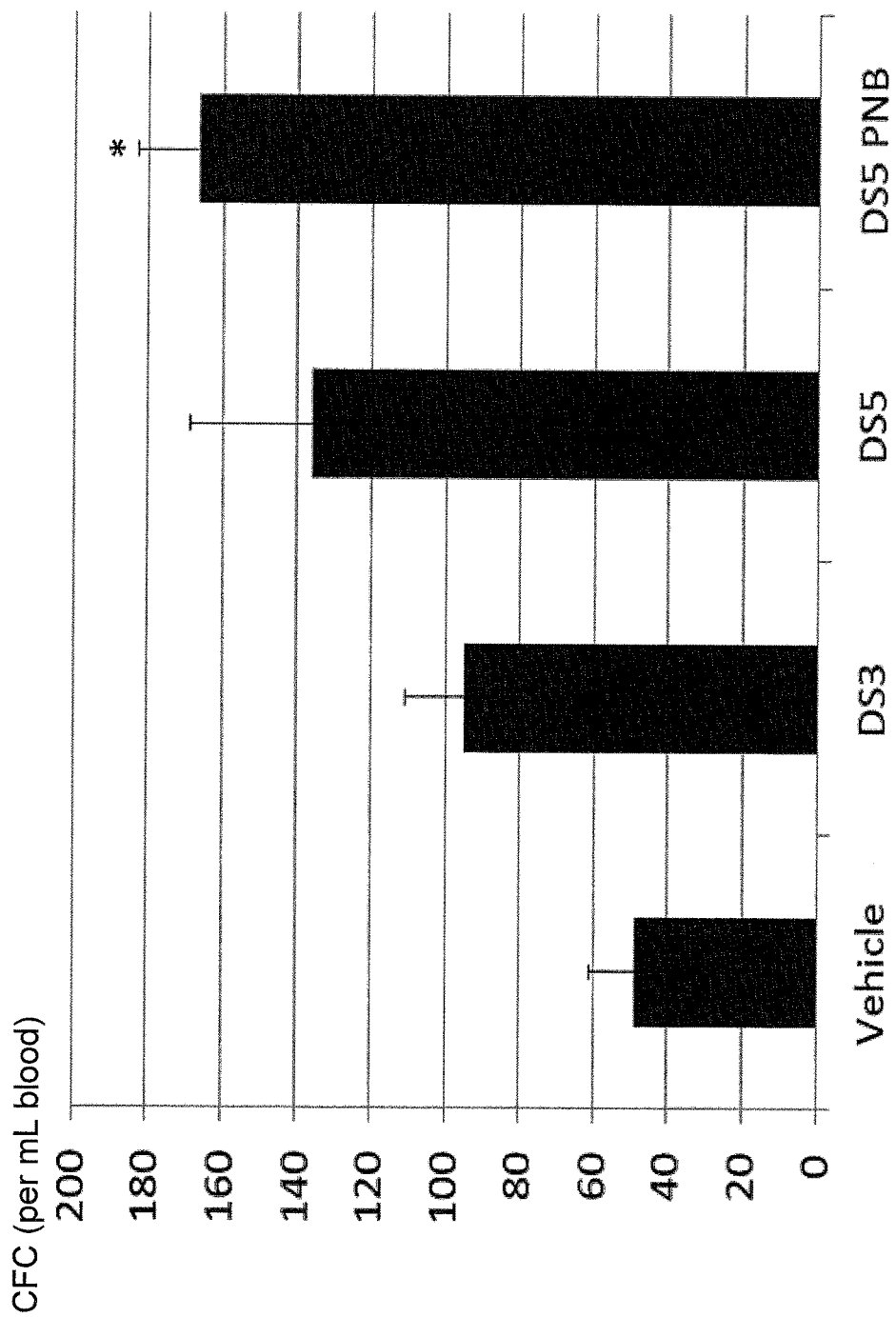
FIG. 11 illustrates the efficacy of dextran sulfate on mobilizing hematopoietic progenitor cells into peripheral blood. Animals were treated with a single i.v. injection of dextran sulfate of different average molecular weight (DS3 or DS5) or with vehicle (NaCl). Error bars show SEM. Student t-test was used to evaluate statistically significant differences compared to control group (*$p<0.05$).
Figure 12:
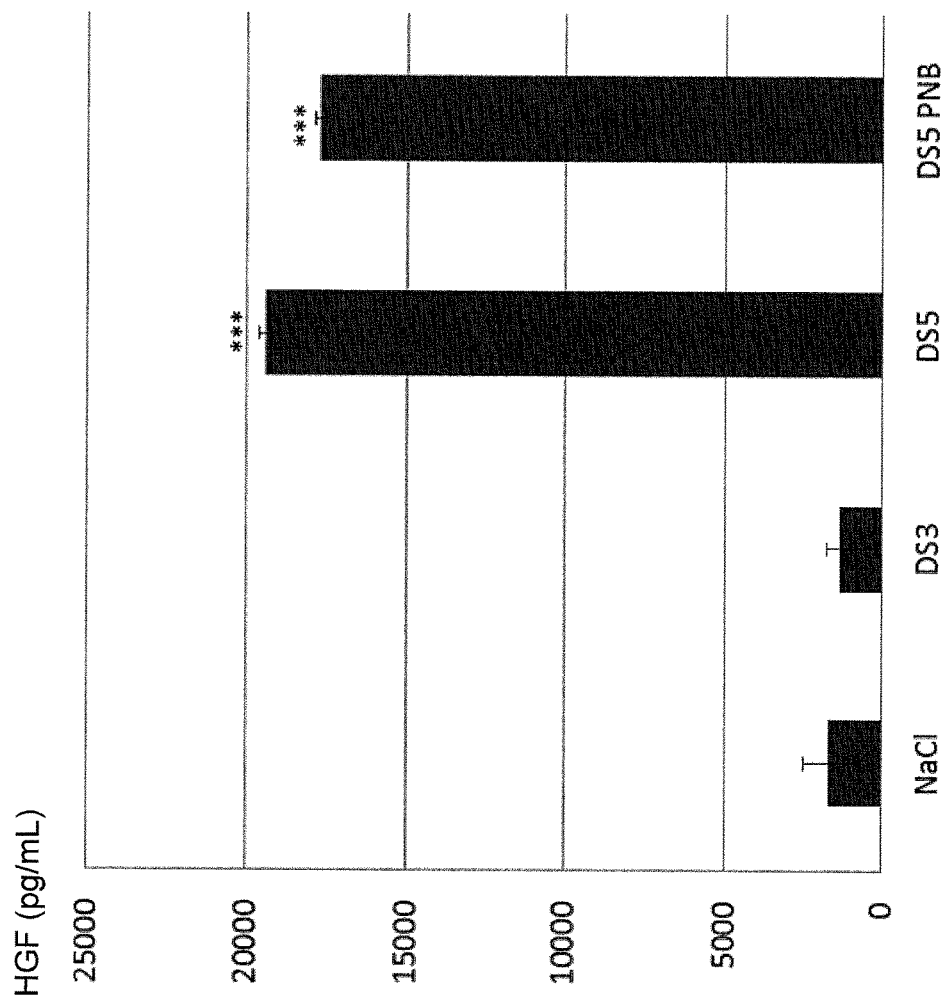
FIG. 12 illustrates the efficacy of dextran sulfate on increasing HGF levels in peripheral blood. Animals were treated with a single i.v. injection of dextran sulfate of different average molecular weight (DS3 or DS5) or with vehicle (NaCl). Error bars show SEM. Student t-test was used to evaluate statistically significant differences compared to control group (***$p<0.001$).
Figure 13:
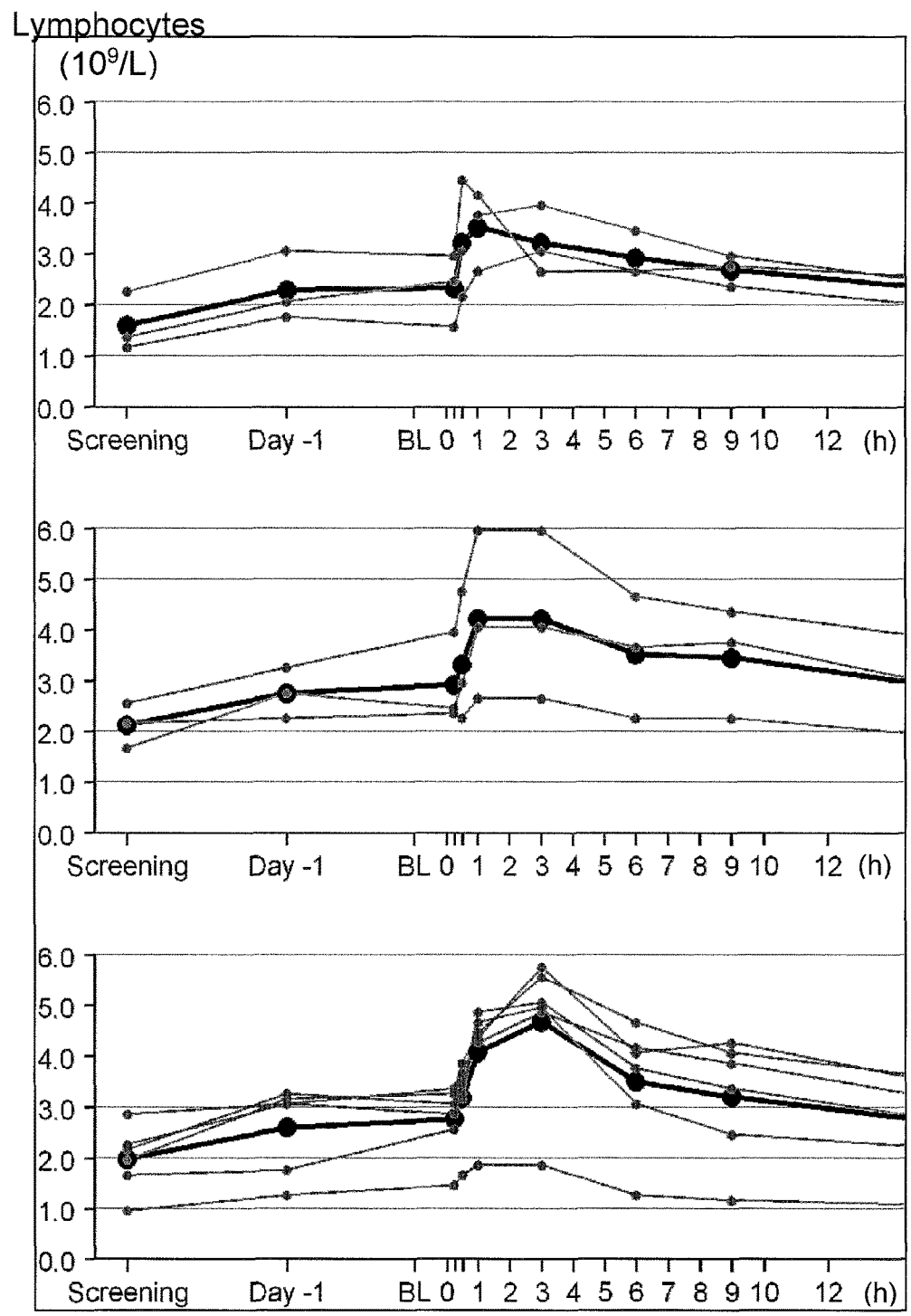
FIG. 13 illustrates mobilization of lymphocytes in peripheral blood in humans receiving a 10 min i.v. infusion of 15 mg/kg LMW-DS (top panel), 18 mg/kg LMW-DS (middle panel) or 24 mg/kg LMW-DS (lower panel) at time 0. The black line represents average lymphocyte levels and gray lines represent lymphocyte levels in individual humans.

Experimental data as presented herein demonstrate that there is a lower limit with regard to the average molecular weight of dextran sulfate in order to have any cell mobilizing effect, see FIGS. 10 and 11. Thus, dextran sulfate molecules having an average molecular weight below the range of the present embodiments do not show any significant positive effect with regard to mobilizing progenitor and/or stem cells, or indeed with regard to mobilizing white blood cells, in particular lymphocytes, or inducing hepatocyte growth factor (HGF), see FIGS. 10-12.

Dextran sulfate molecules having an average molecular weight above the range of the present embodiments also have inferior effects with regard to cell mobilization.

Sweeney 2000 and Sweeney 2002 indicated that 10 kDa dextran sulfate was about three times slower than plerixafor in mice in terms of mobilizing progenitor/stem cells with a harvesting time suggested to be 3 hours following dextran sulfate administration as compared to harvesting after 1 hour following plerixafor administration (Broxmeyer 2005). Experimental data presented herein indicates that dextran sulfate having an average molecular weight according to the embodiments almost immediately causes an increase in the number of mobilized colony forming cells (CFCs) and that the peak occurs 7.5-30 minutes following dextran sulfate administration in mice as compared to 1 hour for plerixafor and 3 hours for 10 kDa dextran sulfate. Correspondingly, in human patients the peak in CFC mobilization will occur at about 0.5 to 3 hours, such as about 1 hour following dextran sulfate administration. Hence, CFC mobilization by dextran sulfate performed in humans seems to be about 6-9 times slower in humans than in mice. This inter-species relationship is similar to plerixafor where the peak in CFC mobilization occurs at about 9 hours following plerixafor administration in humans as compared to 1 hour following plerixafor administration in mice.

Hence, the dextran sulfate of the embodiments seems to have significantly faster cell mobilizing effect than what is indicated in the prior art for larger dextran sulfate molecules, see Sweeney 2000 and Sweeney 2002.

Han 1998 investigated dextran sulfate having a molecular weight of 10 kDa and G-CSF with regard to mobilization of white blood cells (WBC), mono-nuclear cells (MNC) and CFU-GM in mice. The authors discussed that the peaks in peripheral WBC, MNC and CFU-GM occur 2-5 hours after i.v. injection of 15-30 mg dextran sulfate 10 kDa in mice. Hence, the mentioned time period is similar to the three hours suggested by Sweeney 2000 and Sweeney 2002.

Han 1998 further compared the post-administration levels of peripheral WBC, MNC and CFU-GM following 10 µg/kg G-CSF given every day for five days (G-CSF group), 15 mg/kg dextran sulfate 10 kDa given once on day 5 (DS group) and 10 µg/kg G-CSF given every day for five days and 15 mg/kg dextran sulfate 10 kDa given once on day 5 (DS+G-CSF group). There was no significant difference in any of the three groups with regard to WBC and MNC. The DS group had a CFU-GM level of 12.9±1.6 colonies with >50 cells, the G-CSF group had a CFU-GM level of 17.1±1.9 colonies, whereas the combined treatment of DS and G-CSF (DS+G-CSF group) had a CFU-GM level of 19.8±2.3, i.e. slightly above the level achieved merely with G-CSF treatment.

Hence, Han 1998 indicated that dextran sulfate having an average molecular weight of 10 kDa resulted in a mobilization peak following 2-5 hours from the time of administration in mice and that the combination of this dextran sulfate with G-CSF had hardly any additional effect over sole G-CSF treatment in mice.

The dextran sulfate having an average molecular weight of the embodiments has a significantly different administration profile and effect as compared to what is disclosed for dextran sulfate 10 kDa in Han 1998. Firstly, the dextran sulfate of the embodiments seems to have significantly faster cell mobilizing effect than what is indicated in the prior art for larger dextran sulfate molecules (7.5-30 minutes versus 2-5 hours). Secondly, the dextran sulfate of the embodiments has a synergistic effect with regard to cell mobilization when combined with G-CSF. Hence, the combination of dextran sulfate and G-CSF treatment as disclosed herein resulted in an increase in mobilized progenitor cells and lymphocytes in peripheral blood that was larger than the combined effect of only using dextran sulfate and only using G-CSF, see FIGS. 6-9. Hence, dextran sulfate with an average molecular weight within the range of the present embodiments has a true synergistic effect when combined with G-CSF.

As a consequence, the selected range with regard to average molecular weight of the dextran sulfate provides a significantly more efficient cell mobilization as compared to dextran sulfate molecules having an average molecular weight outside of the inventive range of the present embodiments.

Experimental data as presented herein demonstrates that dextran sulfate of the embodiments not only mobilizes about the same total number of progenitor and stem cells, in terms of total number of CFCs, as plerixafor, but dextran sulfate administration can be synergistically combined with other substances, such as G-CSF, to achieve significantly higher levels of total number of CFCs as compared to corresponding combinations of plerixafor and G-CSF. Furthermore, the CFC mobilization profile of dextran sulfate differs from the CFC mobilization with plerixafor. In particular, dextran sulfate of the embodiments is capable of achieving higher levels of the CFU-GEMM and BFU-E CFC types as compared to plerixafor.

The very fast cell mobilization triggered by administration of dextran sulfate of the embodiments enables a fundamentally different administration versus effect profile as compared to plerixafor due to the much faster CFC mobilization. Thus, in this aspect the administration of the dextran sulfate of the embodiments is preferably coordinated and synchronized with regard to the desired timing of achieving a peak in mobilized CFC. For instance, if the mobilized CFC are to be harvested from the peripheral blood of a subject, the administration of dextran sulfate is preferably coordinated and synchronized to occur from about 0 hours to about 8 hours, more preferably from about 0 hours to about 6 hours prior to (before) the start of the CFC harvest for a human subject. More preferably, the dextran sulfate administration occurs from about 0 hours to about 4 hours prior to the start of the CFC harvest.

Harvest of CFC cells following a combined treatment with plerixafor and G-CSF occurs during about 4 hours per harvesting occasion and therefore is coordinated from 9 hours up to 13 hours following plerixafor administration.

A corresponding harvesting protocol according to the embodiments could then be to perform a 4 hour CFC harvest from 0 up 4 hours, from 0.25 up to 4.25 hours, from 0.5 up to 4.5 hours, from 0.75 up to 4.75 hours, from 1 up to 5 hours, from 1.25 up to 5.25 hours, from 1.5 up to 5.5 hours, from 1.75 up to 5.75 hours, from 2 up to 6 hours, from 2.25 up to 6.25 hours, from 2.5 up to 6.5 hours, from 2.75 up to 6.75 hours, from 3 up to 7 hours, from 3.25 up to 7.25 hours, from 3.5 up to 7.5 hours, from 3.75 up to 7.75 hours, from 4 up to 8 hours, from 4.25 up to 8.25 hours, from 4.5 up to 8.5 hours, from 4.75 up to 8.75 hours, from 5 up to 9 hours, from 5.25 up to 9.25 hours, from 5.5 up to 9.5 hours, from 5.75 up to 9.75 hours, from 6 up to 10 hours, from 6.25 up to 10.25 hours, from 6.5 up to 10.5 hours, from 6.75 up to 10.75 hours, from 7 up to 11 hours, from 7.25 up to 11.25 hours, from 7.5 up to 11.5 hours, from 7.75 up to 11.75 hours or from 8 up to 12 hours following dextran sulfate administration. In a preferred embodiment, the start of cell harvest preferably occurs about 0.5 hours, 0.75 hours, 1 hour, 1.25 hours, 1.5 hours, 1.75 hours, 2 hours, 2.25 hours, 2.5 hours, 2.75 hours, 3 hours, 3.25 hours, 3.5 hours, 3.75 hours or 4 hours after administration of dextran sulfate.

Thus, in a particular embodiment the harvest of stem and/or progenitor cells with dextran sulfate induced cell mobilization is advantageously already completed before the CFC harvest has even started when using plerixafor as mobilization inducing agent.

Preliminary human data indicates that cell mobilization with dextran sulfate peaks at about 1 hour following dextran sulfate administration and starts to decline at about 6 hours following dextran sulfate administration and is back to normal levels at least about 24 hours following dextran sulfate administration. Thus, the peak in cell mobilization starts about 1 hour after dextran sulfate administration, which is shown in FIG. 15 exemplified by mobilization of lymphocytes following administration of different doses of dextran sulfate to human subjects at time 0 hours. Thus, the peak effect in cell mobilization in humans typically occurs within the first three hours following dextran sulfate administration.

Thus, dextran sulfate administration leads to a faster and more efficient mobilization of cells as compared to plerixafor and therefore the number of apheresis days required to retrieve the desired amount of mobilized cells will decrease. For subjects with insufficient cell-count, at scheduled apheresis visit, treatment with dextran sulfate aims to secure immediate mobilization of cells and the apheresis can be started as planned. It will facilitate the planning in the apheresis centers and reduce the number of subjects who must undergo multiple mobilization procedures.

Studies performed with dextran sulfate as presented herein have documented an immediate mobilization of progenitor cells. Thus, the number of CFCs peaks already 7.5 minutes after administration with a long-lasting peak persisting for at least 1 hour in mice. The mobilization of HSC using dextran sulfate seems to be more rapid compared to the current mobilization regime including plerixafor treatment, which has a distinct peak at 1 hour in mice:

A rapid, efficient and predictable mobilization of HSC would reduce the hospitalization time for the patient. This would also benefit the apheresis centers due to less apheresis appointments and fewer cancelled sessions due to too low cell counts.

A possible mechanism of action behind the more rapid mobilizing effects of dextran sulfate, which is different compared to plerixafor, is presented below. Briefly, dextran sulfate binds to the heparin-binding domain on BM stromal cells, which releases stromal cell-derived factor 1 (SDF-1) and HSC into peripheral blood. Plerixafor on the other hand affects the SDF-1 gradient by acting as a SDF-1 antagonist, leading to increased amounts of HSC in the peripheral blood. The difference in time in rupturing the SDF-1 gradient suggests different mechanisms of action for the mobilizing substances. The suggested mechanism for dextran sulfate can be explained by binding to a specific sequence of positively charged amino acids termed the heparin-binding domain on the otherwise negatively charged heparan sulfate (HS). This causes a release of SDF-1 into circulation and elevated serum concentration (Sweeney 2002 and Pablos 2003).

The exact mechanisms that control homing and mobilization of HSC to and from the bone marrow are not known but particularly the cytokine SDF-1 and its receptor CXCR4 play a pivotal role. HSC expresses CXCR4 and SDF-1 is produced by the bone marrow. SDF-1 is anchored to proteoglycans (PG) on the membrane of stromal cells, endothelial cells, and the extracellular matrix.

Dextran sulfate disrupts the SDF-1 gradient with increased levels in blood and decreased levels in BM in both mice and non-human primates. The increase of SDF-1 is probably due to the competitive displacement with dextran sulfate from heparan sulphate proteoglycans (HSPG) that sequester the chemokine on endothelial cell surfaces or extracellular matrix in BM and other tissues. In monkeys, a single injection of dextran sulfate resulted in maximum levels of peripheral SDF-1 after 6 hours that returned to baseline after 24 hours (Sweeney 2002). Plerixafor on the other hand binds to the receptors of SDF-1, CXCR4 and CXCR7 (Kalatskaya 2009) and thereby disrupts the binding to SDF-1 in the bone marrow stroma and releasing the cells. Plerixafor affects this SDF-1 gradient by acting as a SDF-1 antagonist, leading to increased amounts HSC in the peripheral blood (Broxmeyer 2005 and Lapidot 2003).

In addition to achieving a significantly faster cell mobilization as compared to plerixafor, dextran sulfate administration also achieves different stem or progenitor cell mobilization profiles. In particular, dextran sulfate provides higher levels of the CFC types BFU-E and CFU-GEMM as compared to plerixafor. This cell mobilization profile of the embodiments can have several clinical benefits. For instance, it has been established that the number of infused CFU-GEMM to the patient is correlated to the time for recovery of neutrophils and platelets (Roodman 1987). Hence, transplantation of HSC with increased CFU-GEMM content would decrease the critical time period with an increased risk of infections for the patient and would be of great benefit to the patient. Also increased levels of BFU-E in the mobilized cells will be beneficial in cell transplantations. It has been demonstrated that the number of infused BFU-E cells during the cell transplantation improved neutrophil and platelet recovery and hematopoietic recovery (Cooper 1997 and Hassan 1997).

Stem and/or progenitor cells mobilized by dextran sulfate administration according to this aspect can be harvested according to techniques well known in the art, such as apheresis. Briefly, intravenous tubes are connected to the patient in order to continually circulate the patient's blood through an apheresis machine and then back to the patient. The apheresis machine then separates different types of blood and immune cells.

The harvested stem and/or progenitor cells can be used in allogenic or autologous transplantation, such as HSCT.

The harvested stem and/or progenitor cells can then be infused to a recipient, which is either the patient self (autologous transplantation) or another patient (allogenic transplantation). Today, there are several diseases and disorders where stem and/or progenitor cell transplantation is a therapy. For instance, allogenic transplantation have been suggested to treat various malignancies and cancer diseases including acute myeloid leukemia (AML), acute lymphoblastic leukemia (ALL), chronic myeloid leukemia (CML), myelodysplastic syndromes (MDS), myeloproliferative disorders (MPD), non-Hodgkin'lymphoma (NHL), Hodgkin's disease (HD), chronic lymphocytic leukemia (CLL), multiple myeloma (MM) and juvenile chronic myeloid leukemia. Correspondingly, autologous transplantation has been suggested for the following malignancies MM, NHL, HD, AML, neuroblastoma, ovarian cancer and germ-cell tumors. Other cancer diseases include hairy cell leukemia (HCL), acute promyelocytic leukemia (APL) and other myelomas, leukemias and lymphomas.

Even though HSCT is a therapy used primarily for hematologic and lymphoid cancers it is an alternative in a variety of other acquired and congenital conditions including aplastic anemia, paroxysmal nocturnal hemoglobinuria, Fanconi's anemia, Blackfan-Diamond anemia, Thalassemia major, sickle cell anemia, severe combined immunodeficiency, Wiskott-Aldrich syndrome, inborn errors of metabolism, autoimmune disorders and amyloidosis (Copelan 2006).

In addition, since dextran sulfate has an increased mobilization effect on blood cells and performs its effects through a different mechanism of action than the currently used mobilization agent, plerixafor, treatment with dextran sulfate may be useful in all HSCT patients as well as in refractory patients not achieving enough mobilization of stem cells with current therapies.

Dextran sulfate administration not only causes a very rapid and significant increase in mobilization of progenitor and/or stem cells, typically from the bone marrow, into the peripheral blood of a subject. The dextran sulfate of the embodiments additionally has positive effects on several blood parameters immediately after administration and induces a rapid mobilization of white blood cells (WBC). WBC mobilization can be a particular beneficial aspect of the embodiments since the mobilized WBC can reduce the risk of infection and the critical time after a performed HSCT.

A very interesting characteristic of the dextran sulfate according to the embodiments is that the dextran sulfate in particular causes a high mobilization of lymphocytes, significantly higher as compared to plerixafor.

Another aspect of the embodiments therefore relates to dextran sulfate having an average molecular weight in a range of 3500 and 9500 Da, or a pharmaceutically acceptable derivative thereof, for use in mobilizing target white blood cells, in particular lymphocytes, into the blood stream of a subject, preferably a mammalian subject, and more preferably a human subject.

An embodiment of this aspect therefore relates to a method of mobilizing target white blood cells, in particular lymphocytes, into the blood stream a subject, preferably human subject. The method comprises administering of an effective amount of dextran sulfate having an average molecular weight in a range of 3500 and 9500 Da, or a pharmaceutically acceptable derivative thereof, to the subject. Another embodiment of this aspect relates to the use of dextran sulfate having an average molecular weight in a range of 3500 and 9500 Da, or a pharmaceutically acceptable derivative thereof, for the manufacture of a medicament for mobilizing target white blood cells, in particular lymphocytes, into the blood stream of a subject.

The dextran sulfate of the embodiments can be used according to this aspect to mobilize lymphocytes in addition to progenitor and/or stem cells from a subject. However, the dextran sulfate could alternatively be used mainly for mobilizing lymphocytes as target cells to be used in various applications or therapies where lymphocytes are needed.

Any harvest of lymphocytes and the administration of dextran sulfate are preferably coordinated and synchronized as previously described herein for stem and/or progenitor cell mobilization. Hence, dextran sulfate administration is preferably coordinated and synchronized to occur from about 0 to about 8 hours, preferably from about 0 to about 6 hours and more preferably from about 0 hours to about 4 hours prior to the start of lymphocyte harvest for a human subject. The previously disclosed preferred harvesting intervals relative dextran sulfate administration can advantageously also be used for lymphocyte harvest.

Higher infused lymphocyte content has several beneficial advantages in connection with HSCT. For instance, increased amount of lymphocytes infused to a subject together with previously harvested stem and/or progenitor cells will reduce the risk for infections and improve the overall outcome. Higher infused lymphocyte dose predicts higher lymphocyte recovery, which in turn, predicts superior overall survival following autologous hematopoietic stem cell transplantation for MM and NHL patients. Increased lymphocyte dose translates into absolute lymphocyte count at day 15 (ALC-15). It has been concluded that the median overall survival and progression-free survival for NHL patients are significantly better for patients receiving $0.68 \times 10^9$ lymphocytes/kg compared to those receiving $0.34 \times 10^9$ lymphocytes/kg, and similar benefits with higher lymphocyte yield in MM patients (Porrata 2004b).

In clinical trials performed with plerixafor, between 20-25% of HSCT patients experienced infections after transplantation (CHMP Assessment Report Mozobil (plerixafor) Procedure No. EMEA/H/C/001030). Community respiratory viruses have been recognized as a possible cause of serious infections, especially in patients undergoing HSCT. In addition, HSCT recipients with symptomatic upper respiratory infection have a higher tendency to progress to severe pneumonia with a mortality as high as 50-70% (Chemaly 2006). Dextran sulfate of the embodiments may reduce these risks for infections due to the increased levels of lymphocytes.

The mechanism for improved overall survival is proposed to be faster engraftment and reconstitution of lymphocytes, resulting in a stronger graft-versus-tumor (GVT) effect, decreasing residual cancer (Porrata 2004a, 2004b, 2009, and Hiwase 2008). As presented in the experimental results, single administration of dextran sulfate at least doubled the release of lymphocytes in single therapy compared to single administration of G-CSF or plerixafor. Dextran sulfate in combination with G-CSF is approximately twice as efficient in mobilizing lymphocytes as compared to the combination of G-CSF and plerixafor.

The inducing effects on WBC and especially lymphocytes might be based on the underlying mechanism that dextran sulfate has been shown to disrupt the SDF-1 gradient with increased levels of cells in blood and decreased levels in BM in both mice and nonhuman primates (Sweeney 2002). The increase of SDF-1 is probably due to the competitive displacement with dextran sulfate from heparan sulphate proteoglycans that sequester the chemokine on endothelial cell surfaces or extracellular matrix in BM and other tissues. Another possible mechanism is that dextran sulfate interferes with leukocytes by cell-to-cell interactions e.g. leukocyte rolling and selectin-mediated leukocyte adhesion.

Dextran sulfate according to the embodiments can therefore be used in connection with donor lymphocyte infusion (DLI). DLI is an adoptive immunotherapy that is sometimes used after HSCT. In DLI lymphocytes from the original stem cell donor are infused, after the stem and/or progenitor cell transplantation, to augment an anti-tumor immune response or ensure that the donor stem cells remain engrafted. The goal of this therapy is to induce a remission of the patient's cancer by the GVT effect. The donor lymphocytes can thereby attack and control the growth of residual cancer cells.

The dextran sulfate of the embodiments is advantageously used in combination with G-CSF to treat subjects and improve the yield of mobilized cells. As is disclosed in the experimental section, the combined treatment of dextran sulfate and G-CSF synergistically increased the number of mobilized cells, both stem and progenitor cells and various WBC, as compared to treatment with dextran sulfate alone. In addition, the combination of dextran sulfate and G-CSF leads to significantly higher levels of mobilized cells as compared to the combination of plerixafor and G-CSF. The synergistic effect as seen between plerixafor and G-CSF seems to be even more prominent for the combination of dextran sulfate and G-CSF. This was unexpected in particular in the light of Han 1998 where the combination of dextran sulfate 10 kDa and G-CSF gave basically the same result as only using G-CSF.

A further aspect therefore relates to a cell mobilizing composition comprising dextran sulfate having an average molecular weight in a range of 3500 and 9500 Da, or a pharmaceutically acceptable derivative thereof, and G-CSF. Related embodiments of this aspect defines the combined usage of dextran sulfate of the embodiments and G-CSF for mobilizing cells, in particular stem and/or progenitor cells and/or WBC and in particular lymphocytes in a subject, preferably a human subject.

The cell mobilization composition preferably also comprises a vehicle, such as an aqueous solvent.

An embodiment of this aspect therefore relates to a method of mobilizing cells, such as stem and/or progenitor cells and/or lymphocytes, into the peripheral blood of a subject, preferably human subject. The method comprises administering an effective amount of dextran sulfate according to the embodiments, or a pharmaceutically acceptable derivative thereof, and an effective amount of G-CSF or administering the above-mentioned cell mobilizing composition to the subject. Another embodiment of this aspect defines a combination of dextran sulfate according to the embodiments, or a pharmaceutically acceptable derivative thereof, and G-CSF or the above-mentioned cell mobilizing composition for use in mobilizing cells, preferably stem and/or progenitor cells and/or lymphocytes, into the peripheral blood of a subject, preferably a human subject. A further embodiment of this aspect relates to the use of a combination of dextran sulfate according to the embodiments, or a pharmaceutically acceptable derivative thereof, and G-CSF or the above-mentioned cell mobilizing composition for the manufacture of a medicament for mobilizing cells, preferably stem and/or progenitor cells and/or lymphocytes, into the peripheral blood of a subject, preferably a human subject.

The G-CSF used according to this aspect can be from any suitable G-CSF source including recombinant or purified G-CSF. Non-limiting example include NEUPOGEN® (filgrastim which is a G-CSF analog), NEUTROGIN® (lenograstim which is a recombinant G-CSF), NEULASTA® (pegfilgrastim which is a polyethylene glycol form of filgrastim). Biologically active fragments, variants, derivatives or fusion molecules can alternatively or in addition be used as G-CSF source if they have the ability of mobilizing cells similar to native G-CSF.

Currently, G-CSF (10 μg/kg) is administered to the subject each morning for 4 days prior to apheresis and then on each morning of apheresis. This administration protocol can be used also in connection with dextran sulfate of the embodiments. Hence, G-CSF is preferably administered to the subject at one or a few occasions prior to dextran sulfate administration and cell harvest, such as once or twice 1-7 days, such as once or twice 2-4 days prior to apheresis and preferably additionally on the morning of the apheresis day.

Alternatively, or in addition, dextran sulfate administration may take place prior to G-CSF administration. For instance, dextran sulfate according to the embodiments have the additional beneficial effect of inducing HGF when administered to a subject as further discussed here below. It could then be beneficial to have increased HGF levels in the peripheral blood of the subject when G-CSF is administered to the subject. In a preferred embodiment, the dextran sulfate is then administered not only prior to, or indeed together with G-CSF, but is preferably also administered after the end of the G-CSF administration protocol mentioned above.

The combination of dextran sulfate with G-CSF synergistically increased the number of CFC in peripheral blood up to 18000 CFC/mL blood, i.e. more than 100-fold over control and seemingly more efficient as compared to plerixafor in combination with G-CSF. In some patients, treatment with G-CSF in combination with plerixafor does not mobilize sufficient amounts of HSC for a following transplantation. Combining G-CSF with dextran sulfate may improve the yield of HSC in these refractory patients and enable the planned transplantation. The synergistic increase in the number of CFC in peripheral blood with dextran sulfate and G-CSF will be advantageous for patients undergoing autologous stem cell transplantation where it is troublesome to obtain warranted cell counts from the patient to continue with the following transplantation.

Generally, a sufficient number of HSC must be obtained from the donor in the apheresis procedure for a subsequent successful transplantation. In the clinical situation the number of HSC cells is measured as the amount $CD34^+$ cells in the apheresis product. This marker has been shown as a consistent and strong predictor of engraftment after chemotherapy. However, the $CD34^+$ cell population is heterogeneous and the $CD34^+$ marker is only a surrogate marker of HSC function. In general $<2.5\times10^6$ $CD34^+$ cells per kilo is inadequate for a HSCT, and transplantation of $>20\times10^6$ $CD34^+$ cells may generate engraftment syndrome, which is a toxicity of stem cell transplantation that occurs unexpectedly and is occasionally fatal. Between these numbers there is documentation that supports that the more cells retrieved the better transplantation outcome, since engraftment is faster, hospitalization time is reduced and thereby costs are decreased.

In order to succeed with hematopoietic stem cell transplantation, i.e. to secure effective and quick engraftment to avoid infections and to prevent relapse of disease, mobilization of sufficient amounts of peripheral blood stem cells is therefore important.

Irrespective of whether it is an autologous and allogenic transplantation, the primary aim is to achieve successful engraftment. Failure to do this will result in a critical situation which can lead to a patient without hematological and immunological systems. In order to avoid such a life-threatening situation, it has to be assured that the transplant contains enough cells to ensure successful engraftment. If the cell count is too low, the myeloablative therapy will have to be postponed and valuable time is lost. Also after the myeloablative therapy the transplantation with higher numbers of progenitor cells may lead to more rapid engraftment, which may result in a decreased need for hospitalization and supportive care. As mentioned, the standard method for increasing the number of circulating hematopoietic progenitor cells in the blood is to treat the donor with G-CSF for several days. Even with current treatment (plerixafor and G-CSF) all patients do not achieve sufficient cell count to warrant transplantation. In addition, after the transplantation there is a risk for infection and relapse of disease.

For these patients dextran sulfate has the potential to act as rescue therapy or as an alternative to plerixafor and G-CSF.

Apart from its effects on mobilization, the dextran sulfate of the embodiments exerts additional effects that could have favorable implications for the outcome of HSCT. Dextran sulfate induces immediate and elevated plasma levels of hepatocyte growth factor (HGF), a hormone with mitogenic effect on different cell types and that favors engraftment of transplanted cells (Roos 1995 and Zioncheck 1995). HGF also functions as a synergistic proliferative factor on HSC growth when combined with granulocyte/macrophage colony-stimulating factor (GM-CSF) (Kmiecik 1992 and Weimar 1998) as well as colony formation of human cord-blood derived HSC induced by GM-CSF, G-CSF or M-CSF (Goff 1996). HGF have also shown to partially restore hematopoiesis in mice deficient in c-kit/SCF, a signaling system important for the growth and proliferation of primitive hematopoietic cells (Yu 1998). HGF in the presence of erythropoietin induces the formation of erythroid burst-forming unit (BFU-E) colonies from $CD34^+$ cells (Galimi 1994). Our results show that dextran sulfate induces significantly more BFU-E compared to plerixafor, which may be due to the more pronounced elevation in HGF, compared to plerixafor.

Dextran sulfate has, compared with current treatment, the potential to improve the mobilization of progenitor and other blood cells and the following transplantation outcome in several ways which would be of significant benefit to the patient. In general, dextran sulfate has been shown to increase the yield of circulating WBC, lymphocytes, HGF and progenitor cells.

An increased mobilization of these specific cells and growth factors would greatly improve the outcome for the patient since it would improve the result of the transplantation due to a better and faster engraftment of the transplanted cells. Dextran sulfate treatment may reduce the risk for infections since the lymphocyte content and CFU-GEMM seems to be increased, which may shorten the time of neutropenia. This will also imply a shorter hospitalization time for the patient. In addition, mobilization with dextran sulfate may enable more patients receiving HSCT.

A more efficient mobilization will reduce the need for repeated cell harvests from the patient and therefore lower the risk of side effects (mainly from long term administration of G-CSF) since the treatment period is shortened. Dextran sulfate increases the total yield of HSCs, which benefits the patient by reaching the minimal amount of mobilized HSC in order to warrant transplantation as well as increasing the prediction for cell harvest.

Engraftment and homing of dextran sulfate treated stem cells has been shown to be more efficient than untreated stem cells in mice (Hayakawa 2009). This suggests that in addition to enabling more transplantations, dextran sulfate has the potential to increase the success rate of HSCT by increasing the predictability of HSC transplantation, reducing complications post HSCT, reducing the need for repeated cell harvest, helping more patients reaching the minimal amount of cells to warrant a HSCT and increasing the number of patients receiving successful engraftment after HSCT.

The mechanism for improved overall survival is proposed to be faster engraftment and reconstitution of lymphocytes, resulting in a stronger GVT effect, decreasing residual cancer (Porrata 2009). Administration of dextran sulfate at least doubles the release of lymphocytes in single therapy compared to single administration of G-CSF or plerixafor. Dextran sulfate in combination with G-CSF doubles the release of mobilizing lymphocytes compared to the combination of G-CSF and plerixafor.

Additionally, an increased yield of lymphocytes will also be useful in DLI, useful for allograft transplantation where repeated infusions of lymphocytes are utilized to improve the outcome of the transplantation.

In addition, dextran sulfate causes more than a 100-fold increase of HGF compared to baseline levels and 25 times more than plerixafor, indicating an immediate elevation of HGF (from <160 to 16000 pg/mL) already after 15 minutes. These levels are high enough to induce cell proliferation.

Table 1 below summarizes some of the beneficial effects achieved with dextran sulfate.

TABLE 1 advantages of dextran sulfate treatment

| Assumed significant benefit for the patient | Preclinical effects with dextran sulfate |
|---|---|
| Increased cell engraftment, transplantation outcome, and overall survival. | Increased number of progenitor cells. Dextran sulfate treated cells show increased engraftment. Seemingly more CFU-GEMM progenitors. |
| Reduced risk of infection. | Increased number of lymphocytes. Increased number of progenitor cells. |
| Predictability of mobilization and cell harvest. | Rapid mobilization. Increased number of progenitor cells. |
| Shorter hospitalization time. | Increased number of lymphocytes. Increased number of progenitor cells. Seemingly more CFU-GEMM progenitors. |
| Less G-CSF side effects. | Increased number of progenitor cells. |
| Increased GVT effect. | Increased number of lymphocytes. |

The mobilization of progenitor and/or stem cells and/or target white blood cells, optionally together with HGF, using dextran sulfate according to the embodiments may have medical and clinical uses other than harvesting the cells from the subject receiving the dextran sulfate administration. Thus, the mobilization of the cells into the peripheral blood of the subject may be used according to various medical applications as mentioned in the foregoing. For instance, HSC mobilized into the peripheral blood of a human subject can be used to treat, prevent or at least reduce symptoms of a variety of autoimmune disease including, but not limited to, rheumatoid arthritis (RA), systemic lupus erythematosis (SLE), type 1 diabetes, multiple sclerosis (MS), amyotrophic lateral sclerosis (ALS), Sjögren's syndrome and inflammatory bowel disease. Other uses of stem and/or progenitor cells immobilized into the peripheral blood can be to induce tissue and organ repair, including heart repair.

Also mobilization of target white blood cells, such as lymphocytes, into the peripheral blood of a subject could be used in various medical applications. For instance, raising the level of lymphocytes in the peripheral blood could be used to treat, prevent or at least reduce symptoms of a variety of solid and hematologic cancers including, but not limited to, chronic lymphocytic leukemia (CLL) and breast cancer.

Thus, administration of dextran sulfate according to the embodiments does not necessarily have to be used in order to mobilize cells for the purpose of harvesting the cells from the subject. The administration of dextran sulfate can instead be used with the purpose of achieving an increased level or amount of the desired cells in the peripheral blood of the subject, where the cells may exert a desired function in the subject.

The dextran sulfate according to the embodiments is a low molecular weight dextran sulfate (LMW-DS) having an average molecular weight within the range of 3500 and 9500 Da.

In a particular embodiment, the dextran sulfate has an average molecular weight in a range of 4500 and 7000 Da. More preferably, the dextran sulfate has an average molecular weight in a range of 4500 and 5500 Da, such as an average molecular weight of 4.6 kDa, 4.7 kDa, 4.8 kDa, 4.9 kD, 5.0 kDa, 5.1 kDa, 5.2 kDa, 5.3 kDa or 5.4 kDa.

An example of dextran sulfate that can be used according to the embodiments has an average molecular weight of 5139 Da and a polydispersity index (PDI) of 1.2009.

In a particular embodiment, the dextran sulfate has a substantially narrow molecular weight distribution. In such an embodiment, most of the dextran sulfate molecules have a respective molecular weight within the preferred range of 3500 and 9500 Da. In an example embodiment, less than 20% of the dextran sulfate molecules have a molecular weight above 8000 Da, preferably less than 15%, such as less than 10% or less than 5% of the dextran sulfate molecules have a molecular weight above 8000 Da. In addition, or alternatively, less than 40% of the dextran sulfate molecules have a molecular weight below 3000 Da, preferably less than 35%, such as less than 30% or less than 25% of the dextran sulfate molecules have a molecular weight below 3000 Da.

Dextran sulfate is a polyanionic derivate of dextran and contains sulfur. The average sulfur content for dextran sulfate is preferably 15 to 20% and more preferably approximately 17%, generally corresponding to about two sulfate groups per glucosyl residue. In a particular embodiment, the sulfur content of the dextran sulfate is preferably equal to or at least close to the maximum possible degree of sulfur content of the dextran molecules.

The dextran sulfate according to the embodiments can be provided as a pharmaceutically acceptable derivative of dextran sulfate. Such pharmaceutically acceptable derivatives include salts and solvates of dextran sulfate, e.g. a sodium or potassium salt.

Dextran sulfate or a pharmaceutically acceptable derivative thereof is preferably administered by injection to the subject and in particular by intravenous (i.v.) injection, subcutaneous (s.c.) injection or (i.p.) intraperitoneal injection, preferably i.v. or s.c. injection. Other parenteral administration routes that can be used include intramuscular and intraarticular injection. For these administration routes, the dextran sulfate is preferably provided in a formulation in liquid form with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline. Furthermore, other buffer systems than CAM could be used if a buffered solution are desired.

The embodiments are not limited to injections and other administration routes can alternatively be used including orally, nasally, bucally, rectally, dermally, tracheally, bronchially, or topically. The active compound, dextran sulfate, is then formulated with a suitable excipient or carrier that is selected based on the particular administration route.

Suitable dose ranges for the dextran sulfate may vary according to the size and weight of the patient, the condition for which the patient is treated, and other considerations. In particular for human subjects, a possible dosage range could be from 1 μg/kg to 150 mg/kg of body weight, preferably from 0.1 mg/kg to 50 mg/kg body weight, more preferably from 0.25 to 50 mg/kg body weight. Illustrative examples include from 0.3 mg/kg to 50 mg/kg of body weight, 1 mg/kg to 50 mg/kg of body weight, and more preferably from 5 mg/kg to 25 mg/kg of body weight, such as from 5 mg/kg to 20 mg/kg body weight or from 5 mg/kg to 15 mg/kg body weight. Also lower concentration could be used, such as 0.5-5 mg/kg body weight.

The dextran sulfate of the embodiments can be administered at a single administration occasion, such as in the form of a single bolus injection. This bolus dose can be injected quite quickly to the patient but is advantageously infused over time so that the dextran sulfate solution is infused over a few minutes of time to the patient, such as during 5 to 10 minutes. It is generally expected that a single dose and injection or infusion (or indeed other administration) is sufficient to achieve therapeutic effect in the patient according to the embodiments. It is, though, possible to administer the dextran sulfate in multiple dosages at different administration occasions. For instance, a single bolus injection can be complemented with a prolonged infusion of a dextran sulfate solution.

Dextran sulfate may optionally also be administered at multiple administration occasions, such as prior to administration of G-CSF in addition to at the date of cell mobilization, or prior to and together with administration of G-CSF in addition to at the date of cell mobilization, or together with administration of G-CSF in addition to at the date of cell mobilization. The particular dosages of dextran sulfate used at the different administration occasions may be the same or different. For instance, a lower dextran sulfate dose could be used at the administration occasions prior to and together with administration of G-CSF as compared to the dose used at the date of cell mobilization.

EXPERIMENTS

A series of experiments in mice were performed in order to characterize the effects of dextran sulfate on mobilization and to gain additional knowledge about suitable doses, time of harvest, mode of administration, and the effect compared to current treatment using plerixafor (AMD3100) in combination with G-CSF (NEUPOGEN®).

Mice

Female DBA/2 mice were obtained from Harlan Laboratories (Netherlands) and Charles River laboratories (Germany). All animal were kept at the animal facility at Uppsala University, housed under standard conditions and provided food and water ad libitum according to institutional guidelines. Animals 7-40 weeks of age weighing 17-31 g were used. All experiments were approved by the local Animal Ethics Committee, Uppsala, Sweden.

Mobilization Protocol

G-CSF (NEUPOGEN®, Amgen, Holland) was supplied as sterile isotonic aqueous solution at 0.3 mg/mL and was diluted in normal saline to a concentration of 50 μg/mL. G-CSF was administered at a dose of 2.5 μg as a single subcutaneous injection, morning and evening Day -2 and Day -1. Dextran sulfate of different average molecular weights were used:

Meito—an average molecular weight of 6 939 Da provided by Meito Sangyo co Ltd (Tokyo, Japan) and was dissolved in citric acid monohydrate (CAM) buffer;

pKC—an average molecular weight of 5 139 Da provided by pK Chemicals A/S (Copenhagen, Denmark) and was dissolved in CAM buffer or 0.9% NaCl (Fresenius Kabi); and TdB—an average molecular weight of 3.3 kDa provided by TdB consultancy (Uppsala, Sweden) and was dissolved in 0.9% NaCl (Fresenius Kabi).

AMD3100 was purchased from Sigma Aldrich (Germany) and was dissolved in normal saline to a concentration of 2 mg/mL. Day 0 the mice were administrated 100 mg/kg dextran sulfate i.v. or s.c. or 5 mg/kg AMD3100 s.c. unless otherwise specified. In the control group, the animals were administrated CAM buffer or 0.9% NaCl i.v. or s.c. All animal received approximately 50-100 μL of each solution (2.5-5 mL/kg).

Meito Sangyo co Ltd batch N-3188 had the following molecular weight distribution:

| | |
|---|---|
| Mw 0-3000 | 10.61% |
| Mw 3000-8000 | 61.05% |
| Mw 8000-12000 | 19.38% |
| Mw 12000-20000 | 8.15% |
| Mw 20000-30000 | 0.79% |
| Mw 30000-40000 | 0.01% |
| Mp | 5664 Da |
| Mn | 5240 Da |
| AMw | 6939 Da |
| PDI | 1.3242 | pK Chemicals A/S batch 31497 had the following molecular weight distribution:

| | |
|---|---|
| Mw 0-2000 | 3.75% |
| Mw 2000-4000 | 30.62% |

-continued

| | |
|---|---|
| Mw 4000-6000 | 36.64% |
| Mw 6000-8000 | 19.94% |
| Mw 8000-12000 | 8.94% |
| Mw 12000-20000 | — |
| Mw 20000-30000 | — |
| Mw 30000-40000 | — |
| Mp | 4690 Da |
| Mn | 4279 Da |
| AMw | 5139 Da |
| PDI | 1.2009 |

TdB consultancy batch 20341 had the following molecular weight distribution:

| | |
|---|---|
| Mw 0-2000 | 19.26% |
| Mw 2000-4000 | 52.01% |
| Mw 4000-6000 | 26.71% |
| Mw 6000-8000 | 2.01% |
| Mw 8000-12000 | — |
| Mw 12000-20000 | — |
| Mw 20000-30000 | — |
| Mw 30000-40000 | — |
| Mp | 3341 Da |
| Mn | 2557 Da |
| AMw | 3305 Da |
| PDI | 1.2924 |

Mp=peak average molecular weight
Mn=number average molecular weight
AMw=weight average molecular weight Colony-forming Cell Assay Peripheral blood was sampled by terminal heart puncture under isoflurane-anesthesia using EDTA-flushed (0.2 M EDTA prepared from a stock solution of 0.5 M EDTA (prepared by Rudbeck laboratory) diluted 1:2.5 in 0.9% NaCl) syringes.

Blood (100-200 μL) was transferred to polypropylene tubes containing heparin (final concentration 17.5 IE/mL). Erythrocytes were depleted using ammonium chloride solution (StemCell Technologies, Vancouver, BC, Canada). Remaining cells were resuspended in Iscove's modified Dulbecco's Medium with 2% fetal bovine serum (StemCell Technologies) and mixed with 2 mL of methylcellulose media supplemented with a cocktail of recombinant cytokines (MethoCult 3434; StemCell Technologies) and penicillin-streptomycin according to manufacturer's instructions. Cultures of 1.1 mL containing HPCs were plated onto 35 mm dishes (Sarstedt, Landskrona, Sweden) and placed in a humidified chamber with 5% $CO_2$ at 37° C. Total number of colonies was counted on day 12 of culture.

Hematological Analysis

Peripheral blood was sampled by terminal heart puncture under isoflurane-anesthesia using EDTA-flushed syringes and transferred to polypropylene tubes containing 1.6 mg EDTA (Sarstedt, Landskrona, Sweden).

Complete blood counts were obtained using an automated cell counter (Advia 2120 hematology systems; Siemens healthcare diagnostics Inc, Illinois, USA) at the Swedish University of Agricultural sciences (SLU), Uppsala, Sweden.

HGF-ELISA

Peripheral blood was sampled by terminal heart puncture under isoflurane-anesthesia (unless otherwise stated) using EDTA-flushed (0.2 M EDTA prepared as above).

Plasma was prepared by centrifuging EDTA blood for 5 minutes at 3000 g, and frozen at 20° C. until analysis. HGF ELISA assay (RnD systems, Minneapolis, USA) was performed according to instructions from the manufacturer.

Statistics

Data are expressed as mean values plus and minus SEM. Comparison between groups was performed using Student's t-test (two-tailed, equal variance). Statistical analyzes were performed using Microsoft Excel. Differences at a p value less than 0.05 were considered to be statistically significant.

Dextran Sulfate, s.c. Dose Finding Study on Peripheral Blood Cell Mobilization

Mice (DBA/2N, 8-14 weeks, Charles River) were treated with s.c. injections of dextran sulfate (10, 50, 150, and 500 mg/kg, pKC), AMD3100 (5 mg/kg, positive control) or CAM buffer (negative control). The used dose of AMD3100 and 1 hour for cell harvest was the reported optimal dosing regimen for this drug in mice (Broxmeyer 2005). Blood was analyzed using hematological analysis according to above. In more detail, the mice were sacrificed 3 hours after the last injection (1 hour for AMD3100) and hematological differentiation analysis was determined in peripheral blood. Serum and/or plasma samples were collected and stored in −20° C. until analysis. Blood was collected by heart puncture by EDTA-flushed syringes and mixed with EDTA and lepirudin for the cell count analysis and only EDTA for the HGF analysis.

Figure 1:
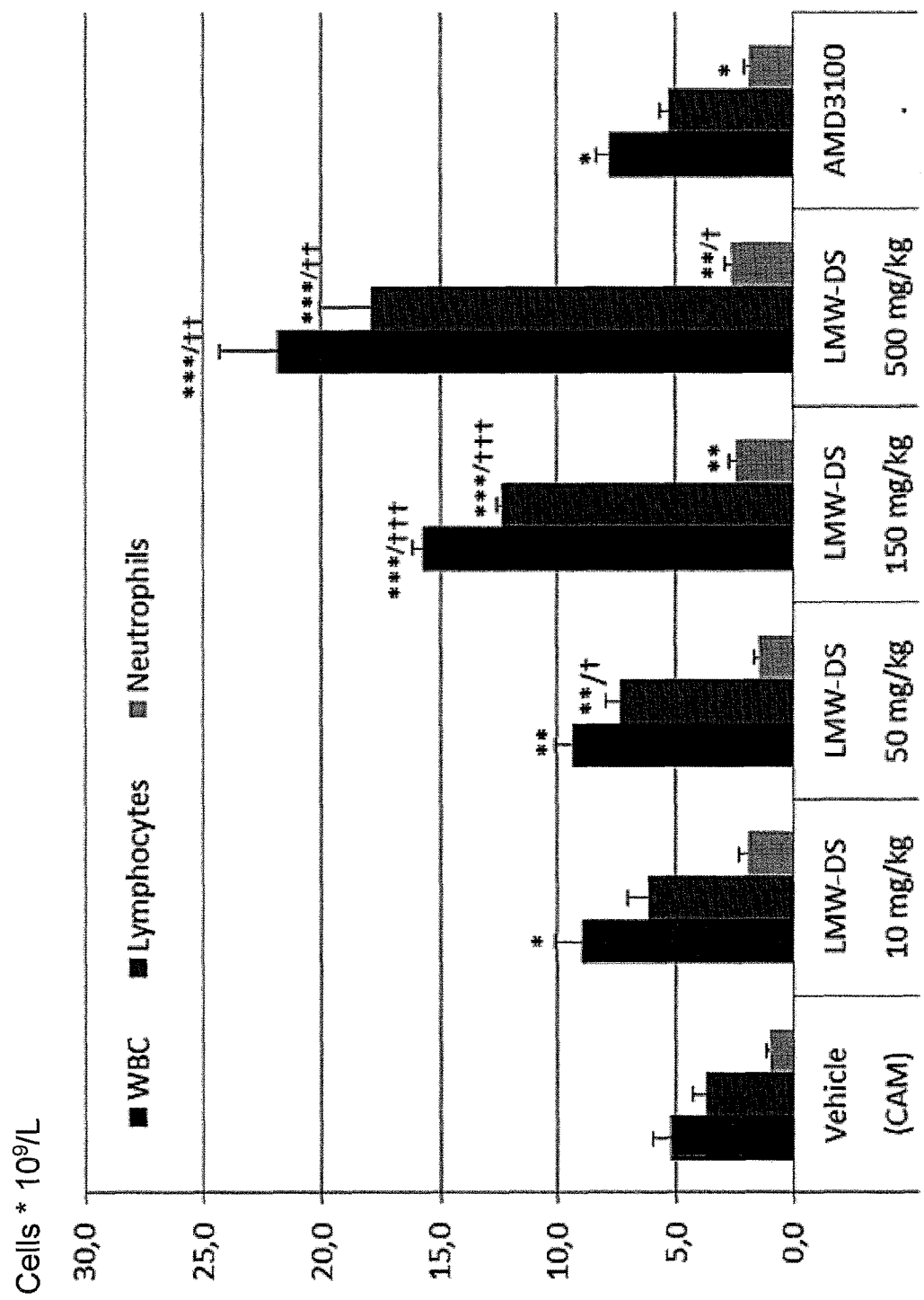
FIG. 1 illustrates leukocyte mobilization induced by single s.c. injection of dextran sulfate (LMW-DS) or AMD3100 compared to control (citric acid monohydrate (CAM)). Blood was sampled after 3 hours (LMW-DS) or 1 hour (AMD3100). Mean±SEM is shown. Statistical analysis compared LMW-DS or AMD3100 to control group (*$p<0.05$, $p<0.01$, *$p<0.001$) or LMW-DS compared to AMD3100 ($^{554}p<0.05$, $^{††}p<0.01$, $^{†††}p<0.001$).
Figure 2:
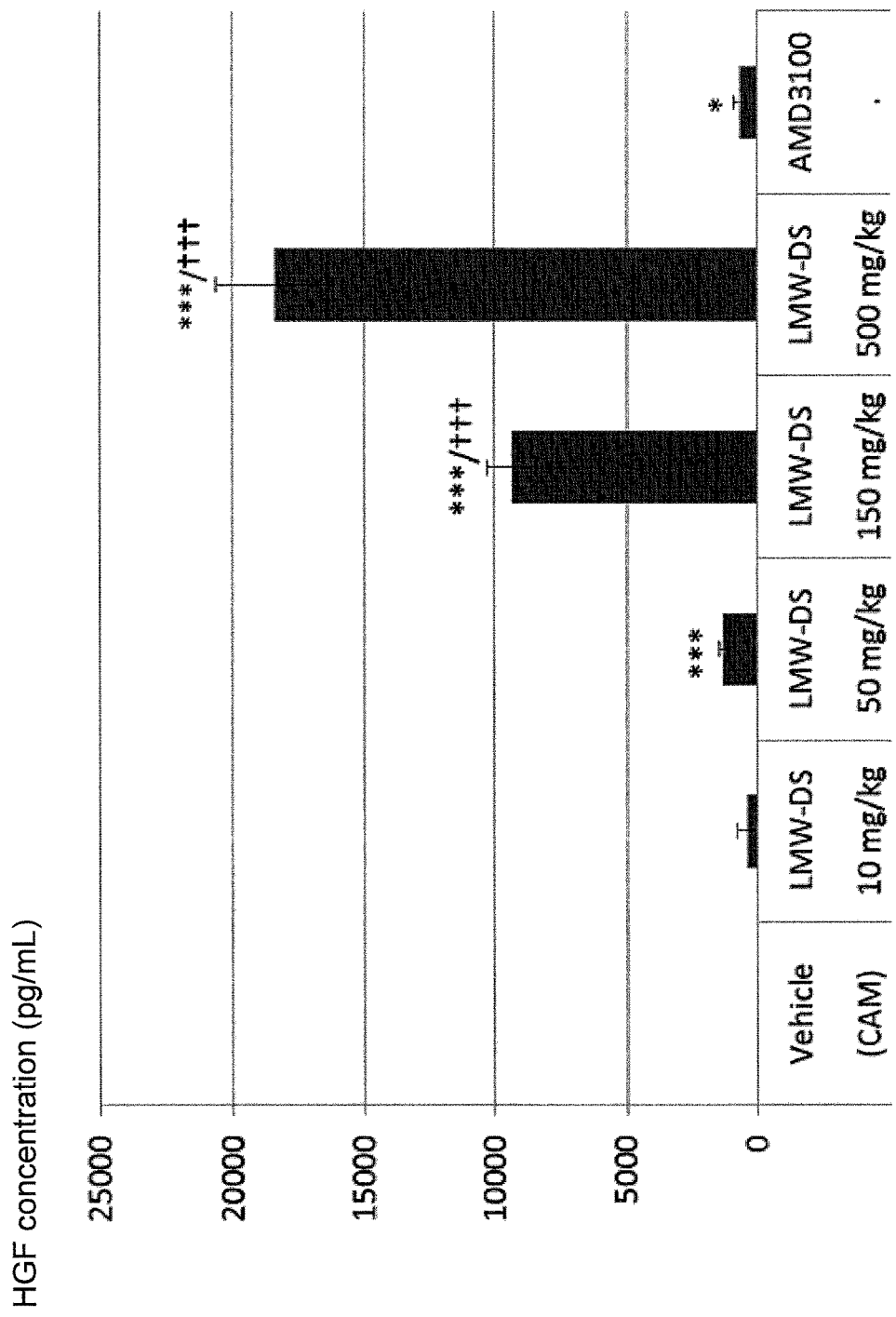
FIG. 2 illustrates the effect of LMW-DS on blood concentration of HGF. The animals were treated with a single s.c. injection of LMW-DS or AMD3100. CAM was used as vehicle control. Blood was sampled after 3 hours (LMW-DS) or 1 hour (AMD3100). Mean±SEM is shown. Statistical analysis compared LMW-DS or AMD3100 to control group (*$p<0.05$, ***$p<0.001$) or LMW-DS compared to AMD3100 ($^{†††}p<0.001$).

There was a dose-dependent increase of circulating white blood cells (WBC), mainly lymphocytes (FIG. 1), and HGF (FIG. 2) at 3 hours after dextran sulfate administration. Doses of 10-50 mg/kg dextran sulfate and AMD3100 5 mg/kg showed similar effects, while the effects of 150 and 500 mg/kg dextran sulfate were significantly increased (p<0.001 and p<0.01 respectively) compared to AMD3100 effect. Administration of dextran sulfate at 50, 150 and 500 mg/kg gave rise to significantly (p<0.001) increased levels (FIG. 2) of circulating HGF which where more pronounced than AMD3100.

Table 2 summarizes the blood parameters after administration of dextran sulfate (LMW-DS) and AMD3100, respectively. The table indicates the hematological variables in peripheral blood after administration of LMW-DS or AMD3100 compared to control (CAM, *p<0.05, p<0.01, *p<0.001) or compared to AMD3100 ($^{554}$ p<0.05, ††p<0.01, †††p<0.001).

TABLE 2

Hematological variables in peripheral blood after administration of LMW-DS

| | Control | LMW-DS 10 mg/kg | LMW-DS 50 mg/kg | LMW-DS 150 mg/kg | LMW-DS 500 mg/kg | AMD3100 |
|---|---|---|---|---|---|---|
| Erythrocytes | 9.1 ± 0.1 | 9.0 ± 0.0††† | 9.2 ± 0.4† | 8.3 ± 0.6 | 9.4 ± 0.2††† | 8.0 ± 0.0*** |
| Hemoglobin | 127.5 ± 1.9 | 122.0 ± 1.7†† | 127.8 ± 5.0† | 113.3 ± 8.2 | 130.3 ± 3.1† | 112.5 ± 0.9*** |
| Hematocrit | 0.4 ± 0.0 | 0.4 ± 0.0† | 0.4 ± 0.0† | 0.3 ± 0.0 | 0.4 ± 0.0†† | 0.3 ± 0.0*** |
| MCV | 42.6 ± 0.3 | 41.9 ± 0.1 | 42.6 ± 0.3 | 41.7 ± 0.4 | 42.4 ± 0.3 | 42.7 ± 0.6 |
| MCHC | 329.3 ± 1.8 | 323.7 ± 3.8 | 324.3 ± 1.41† | 329.3 ± 4.9 | 327.3 ± 2.5 | 332.0 ± 2.0 |

TABLE 2-continued

Hematological variables in peripheral blood after administration of LMW-DS

|  | Control | LMW-DS 10 mg/kg | LMW-DS 50 mg/kg | LMW-DS 150 mg/kg | LMW-DS 500 mg/kg | AMD3100 |
|---|---|---|---|---|---|---|
| Reticulocytes | 202.9 ± 73.5 | 222.7 ± 6.3 | 230.1 ± 64.6 | 243.7 ± 23.7 | 224.5 ± 35.2 | 186.3 ± 23.7 |
| Platelets | 946.8 ± 37.1 | 1083.3 ± 116.3† | 902.0 ± 96.4 | 893.5 ± 60.8† | 893.5 ± 61.0†† | 706.8 ± 30.7** |
| MPV | 8.0 ± 0.1 | 7.7 ± 0.2 | 7.9 ± 0.1 | 7.2 ± 0.5 | 7.9 ± 0.1 | 8.0 ± 0.1 |
| Leukocytes (WBC) | 5.2 ± 0.7 | 9.0 ± 1.2* | 9.4 ± 0.7 | 15.7 ± 0.4***/††† | 21.8 ± 2.5***/†† | 7.8 ± 0.6* |
| Neutrophils | 1.0 ± 0.1 | 1.9 ± 0.4 | 1.5 ± 0.2 | 2.4 ± 0.3** | 2.7 ± 0.3**/† | 1.8 ± 0.2* |
| Eosinophils | 0.1 ± 0.0 | 0.2 ± 0.0† | 0.2 ± 0.0 | 0.3 ± 0.1* | 0.4 ± 0.1* | 0.3 ± 0.0* |
| Lymphocytes | 3.8 ± 0.5 | 6.1 ± 0.5** | 7.3 ± 0.6**/f | 12.4 ± 0.2***/††† | 17.9 ± 2.2***/†† | 5.3 ± 0.4 |
| Monocytes | 0.3 ± 0.0* | 0.6 ± 0.011 | 0.3 ± 0.1 | 0.4 ± 0.0*/†† | 0.5 ± 0.1*/† | 0.3 ± 0.0 |
| LUC | 0.03 ± 0.0* | 0.1 ± 0.0* | 0.1 ± 0.0* | 0.1 ± 0.0***/†† | 0.3 ± 0.2 | 0.05 ± 0.0* |
| Basophils | 0.01 ± 0.0 | 0.02 ± 0.0 | 0.03 ± 0.0 | 0.1 ± 0.0** | 0.1 ± 0.0* | 0.03 ± 0.0 |
| n= | 4 | 3 | 4 | 4 | 4 | 4 |

MCV: mean corpuscular volume
MPV: mean platelet volume
Units: Erythrocytes $10^{12}$ cells/L, other cells $10^9$ cells/L, MCV (fl), MCHC (g/L), HCT (g/L)
MCHC: mean corpuscular hemoglobin concentration
WBC: white blood cells
LUC: lucocytes Dextran Sulfate, i.v. Dose Finding Study on Peripheral Blood Cell Mobilization Mobilization was performed on DBA/2OlaHsd mice (7-12 weeks, Harlan) using 25-200 mg/kg dextran sulfate (Meito) i.v. As positive and negative controls, AMD3100 (5 mg/kg, s.c.) or CAM buffer (i.v.) was used. Blood was analyzed using CFC-assay and hematological analysis according to above.

Figure 3:
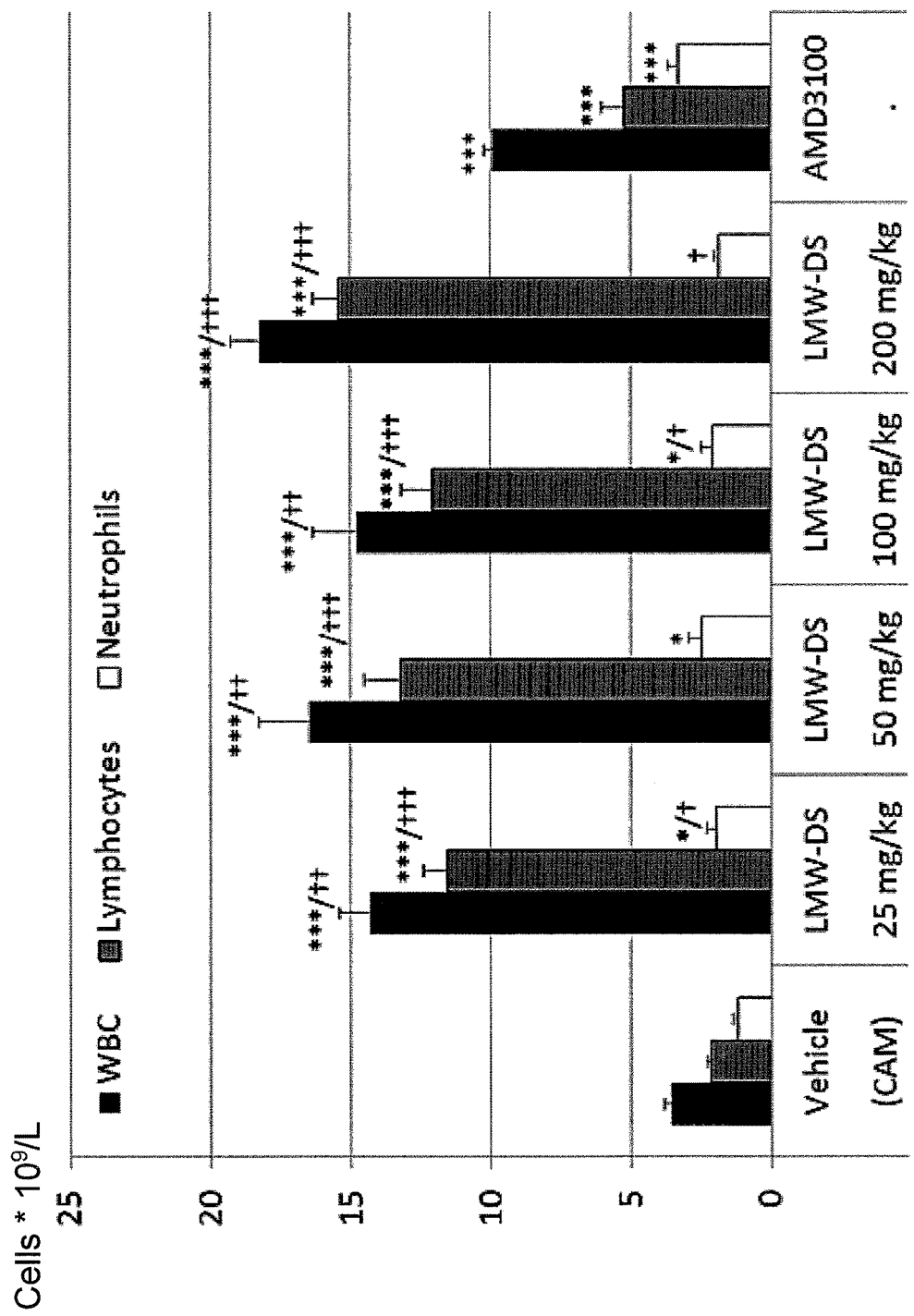
FIG. 3 illustrates leukocyte mobilization to peripheral blood by single i.v. injection of LMW-DS and AMD3100. CAM was used a vehicle control. Blood was sampled after 30 minutes (LMW-DS and vehicle) or 1 hour (AMD3100). Mean±SEM is shown. Statistical analysis compared LMW-DS or AMD3100 to control group (*$p<0.05$, $p<0.01$, *$p<0.001$) or LMW-DS compared to AMD3100 ($^{554}p<0.05$, $^{††}p<0.01$, $^{†††}p<0.001$).

Compared to AMD3100 (5 mg/kg) and control CAM buffer single i.v. injections of dextran sulfate (25, 50, 100, and 200 mg/kg, Meito) induced a significant increase of WBC (p<0.01), mainly of lymphocytes (p<0.001), in peripheral blood already 30 minutes after the dextran sulfate injection (FIG. 3). The mobilization levels achieved with the four doses of dextran sulfate were significantly increased versus AMD3100.

Figure 4A:
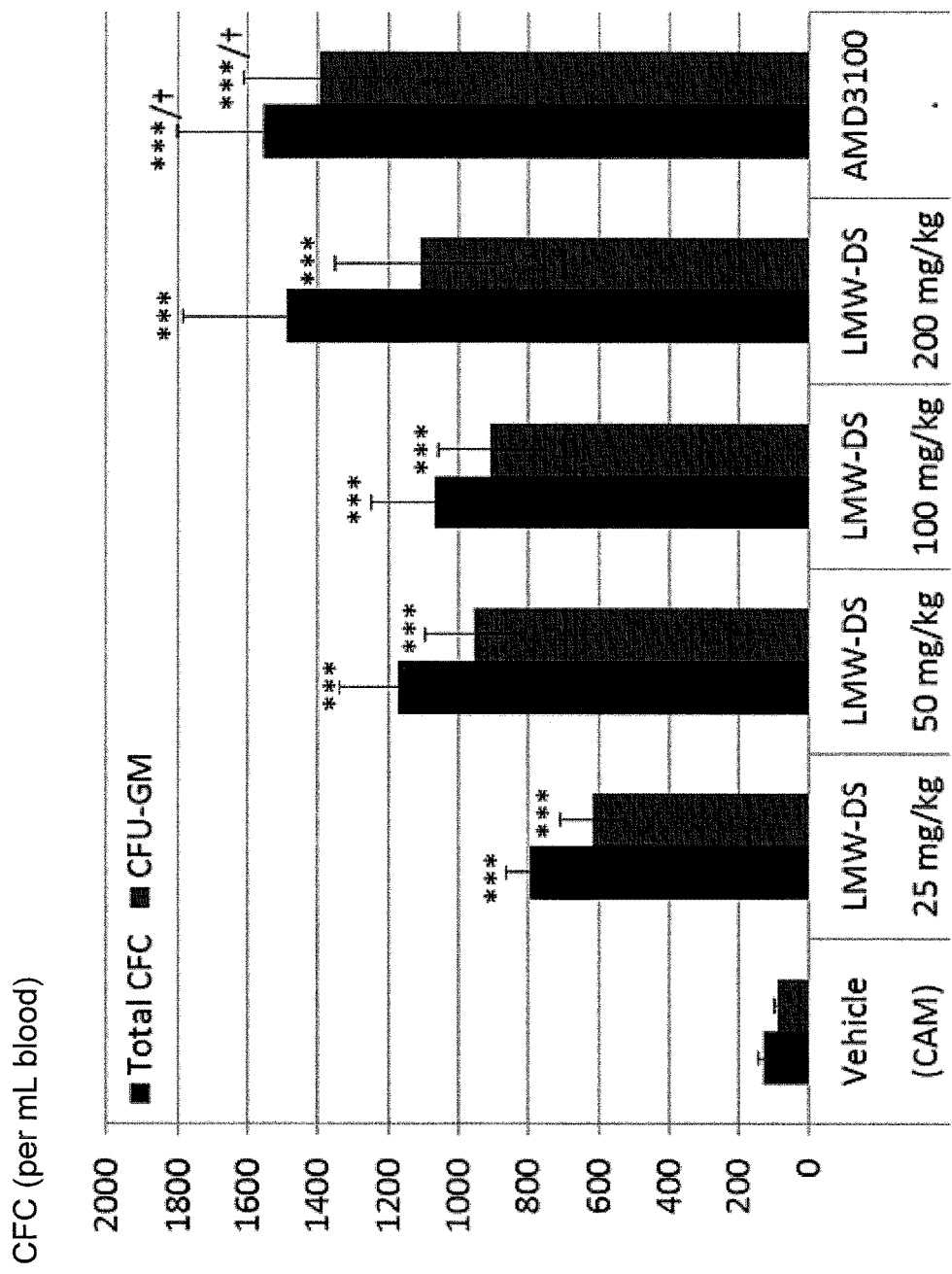
FIGS. 4A and 4B illustrate the effect of single i.v. injection of LMW-DS or s.c. injection of AMD3100 on mobilizing hematopoietic colony-forming cells (CFC) in peripheral blood. CAM buffer (i.v.) was used as vehicle control. Blood was sampled after 30 minutes (LMW-DS and vehicle) or 1 hour (AMD3100). Mean±SEM is shown. Statistical analysis compared LMW-DS or AMD3100 to control group (*$p<0.05$, **$p<0.01$) or LMW-DS compared to AMD3100 ($^{554}p<0.05$)
Figure 4B:
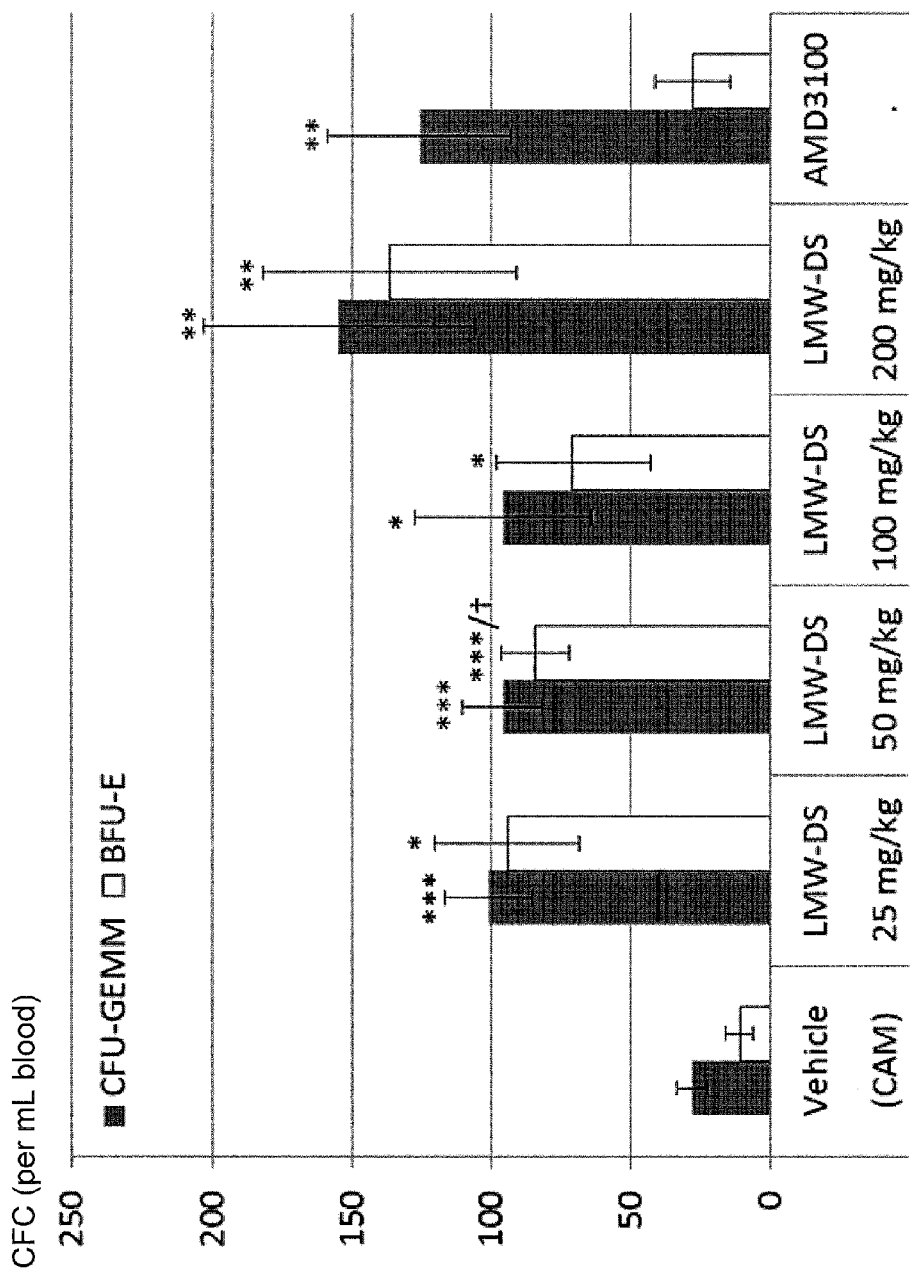

The mobilization effect of dextran sulfate on CFC was also significant evident already at the lowest dose given (25 mg/kg, p<0.001). The effect seemed to increase in a dose-dependent way. The effect after 200 mg/kg of dextran sulfate was similar to that of AMD3100, 5 mg/kg, with regard to total CFC (FIGS. 4A and 4B).

The increase of CFC after single dose administrations of AMD3100 (s.c.) and dextran sulfate (i.v.) was higher (6-12 times over control) compared to the general increase of WBC (3-5 times over control). This might suggest a specific mechanism of action on mobilization of progenitor cells (FIGS. 4A and 4B).

The mobilization effect on the different subtypes of progenitor cells, CFU-GM, CFU-GEMM and BFU-E, was also studied (FIGS. 4A and 4B) and dextran sulfate seemed to increase BFU-E to a greater extent than AMD3100

Dextran Sulfate, Effect of Administration Route on Peripheral Blood Cell Mobilization Mobilization was performed on DBA/2N mice (9-10 months, Charles River) using 100 mg/kg dextran sulfate (Meito, i.v. and s.c.). Blood was analyzed using CFC-assay and hematological analysis according to above.

The effect on peripheral blood cells after administration of 100 mg/kg dextran sulfate i.v. and s.c. was compared (n=5). Cells were harvested 30 minutes after administration for both administration routes. There were no significant differences on circulating WBC, lymphocytes, CFC or CFC subtypes 30 minutes after administration for the different administration routes, see Table 3.

TABLE 3 comparison of blood parameters for s.c. and i.v. administration

|  | s.c. LMW-DS | i.v. LMW-DS |
|---|---|---|
| WBC, *$10^9$/L | 12.5 ± 1.1 | 16.2 ± 1.8 |
| Lymphocytes, *$10^9$/L | 9.9 ± 1.2 | 12.6 ± 1.7 |
| CFC, *$10^9$/L | 692 ± 111 | 712 ± 175 |
| CFC-GM, *$10^9$/L | 604 ± 83 | 592 ± 172 |
| CFC-GEMM, *$10^9$/L | 28 ± 10 | 28 ± 10 |
| BFU-E, *$10^9$/L | 60 ± 22 | 92 ± 12 |

Dextran Sulfate, Time-effect Relationship on Peripheral Blood Cell Mobilization

Mobilization was performed on DBA/2N mice (8-14 weeks, Charles River) using 50 mg/kg dextran sulfate (pKC, i.v.) or 100 mg/kg dextran sulfate (Meito, i.v.). As a negative control CAM buffer (i.v.) was used. Blood was analyzed using CFC-assay, hematological analysis and HGF-ELISA.

Figure 5:
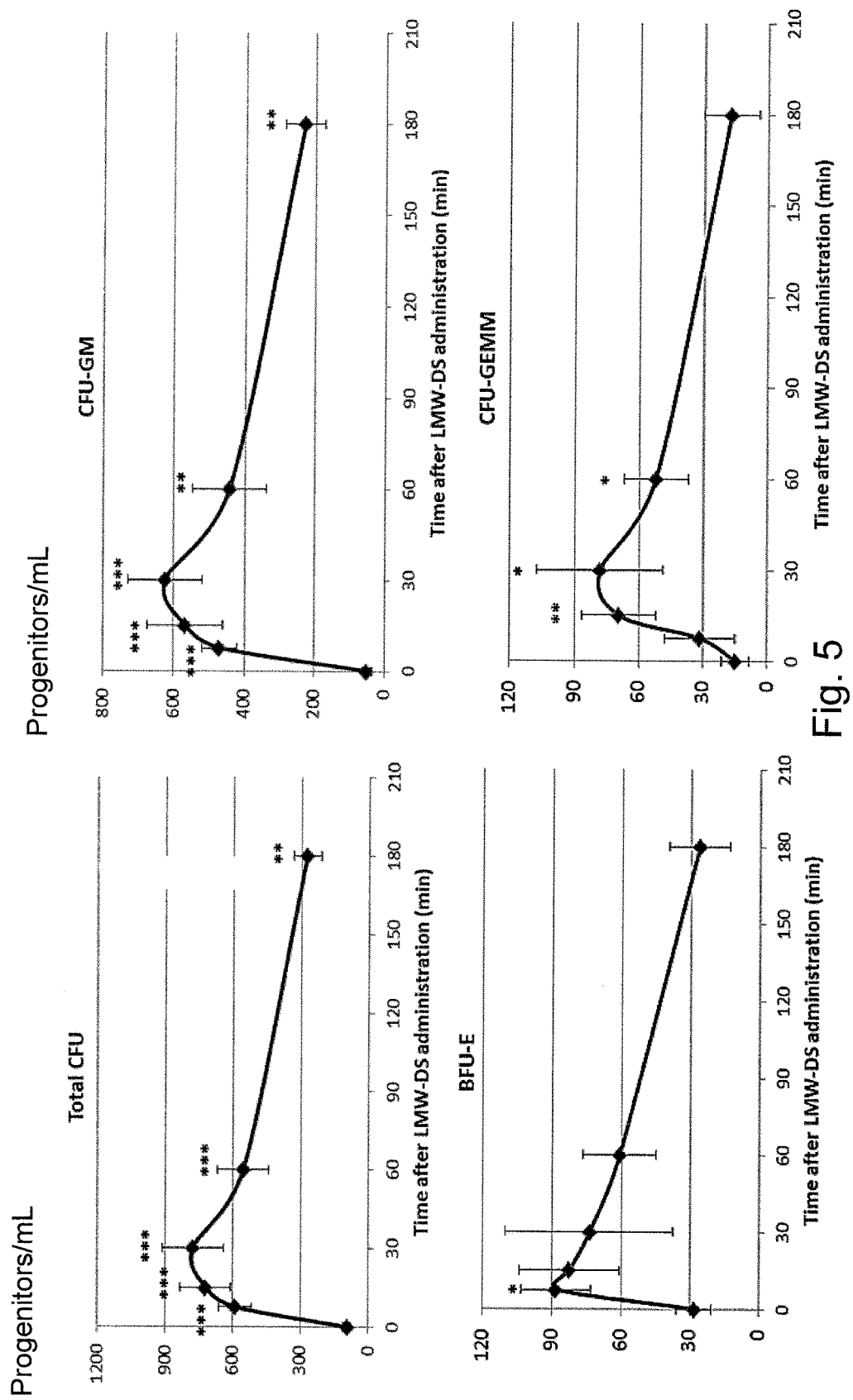
FIG. 5 illustrates a distinction of progenitor subtype (CFU-GM, CFU-GEMM, and BFU-E) of mobilized progenitor cells (CFC) following single i.v. injection with LMW-DS or CAM (control). CAM buffer was used as control and this value was used a 0-value (negative control). Mean±SEM is shown. Statistical analysis compared LMW-DS to control group (*$p<0.05$, $p<0.01$, *$p<0.001$)

The mobilization effect of i.v. administered dextran sulfate (100 mg/kg) showed highest numbers of WBC and lymphocytes around 30 minutes and declined but was still elevated at 3 hours after administration. A very rapid increase of CFC with a peak starting already at 7.5 minutes after administration (FIG. 5) could be seen. The different subtypes of progenitor cells peaked slightly different in time: BFU-E at 7.5 minutes and CFU-GM/CFU-GEMM between 15-30 minutes after administration. HGF was increased to the highest level after 15 minutes (15960 pg/mL) and thereafter subsided. However, HGF was measured in another experiment and not sampled at 7.5 minutes (see Table 4). AMD3100 increased HGF levels to 650±230 pg/mL one hour after administration.

TABLE 4 cell mobilization following dextran sulfate (LMW-DS) i.v. administration

| | CAM | LMW-DS 7.5 min | LMW-DS 15 min | LMW-DS 30 min | LMW-DS 1 hr | LMW-DS 3 hr |
|---|---|---|---|---|---|---|
| WBC,*$10^9$/L | 3.9 ± 0.5 | 5.6 ± 0.5* | 10.2 ± 0.7*** | 14.6 ± 1.3*** | 11.2 ± 0.6*** | 6.8 ± 1.0* |
| Lymph,*$10^9$/L | 2.2 ± 0.2 | 4.6 ± 0.5*** | 8.9 ± 0.7*** | 12.3 ± 1.1*** | 8.8 ± 0.5*** | 5.2 ± 0.8** |
| PLT, *$10^9$/L | 998 ± 34 | 1,034 ± 31 | 1,122 ± 58 | 978 ± 64 | 965 ± 23 | 936 ± 26 |
| HGF, pg/mL | <160 | n.a. | 15,960 ± 1,450*** | 13,800 ± 1,100*** | 7,740 ± 510*** | 710 ± 230** |

Thus, dextran sulfate (100 mg/kg) i.v. administration to mice rapidly increased the number of WBC and in particular lymphocytes (Lymph) in peripheral blood compared to control (CAM). Dextran sulfate did not affect the number of platelets (PLT). Dextran sulfate also quickly increased the amount of HGF in plasma. Results are reported in Table 4 as mean±SEM, n.a.=not analyzed. Statistics presented compared to CAM buffer, *p<0.05, p<0.01, and *p<0.001.

Dextran Sulfate in Combination with G-CSF on Peripheral Blood Cell Mobilization

Standard treatment of patients prior to apheresis is based on daily injections of G-CSF for up to one week. Clinically dextran sulfate could be used in combination with G-CSF. In a study in mice 2.5 µg/animal of G-CSF was administered twice daily (8 hrs apart) for 2 days (Broxmeyer 1999). To investigate the effect of the combination of G-CSF and dextran sulfate, DBA/2OlaHsd mice (10-15 weeks, Harlan) were treated with G-CSF for 2 days (NEUPOGEN®, 2×2.5 µg/day, s.c.) and on day 3 either injected with dextran sulfate (5, 25, 100 mg/kg, Meito, i.v.), CAM (negative control, i.v.) or AMD3100 (positive control, 5 mg/kg, s.c.). Blood was analyzed using CFC-assay and hematological analysis.

Figure 6:
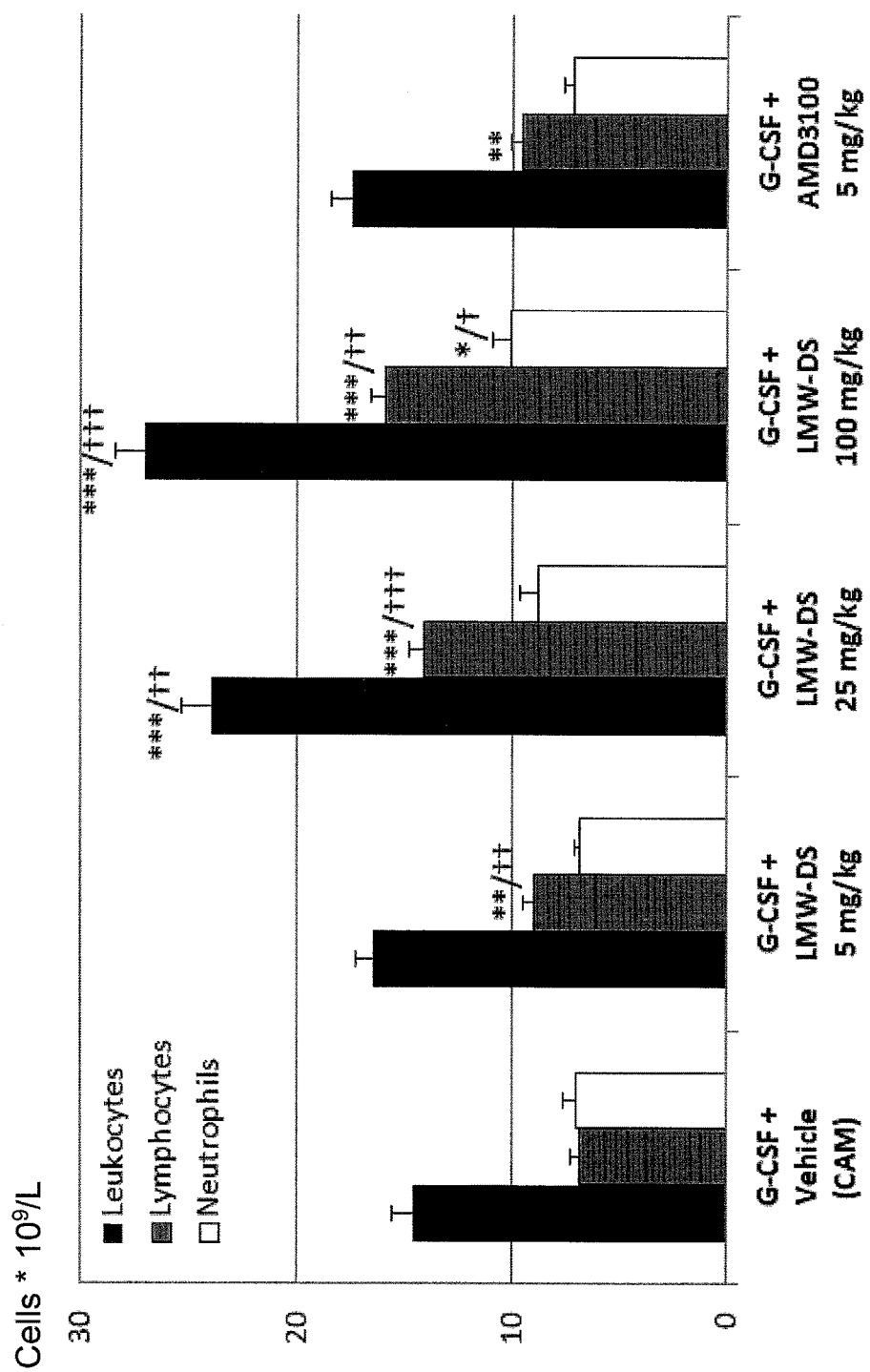
FIG. 6 illustrates leukocyte mobilization induced by combination of G-CSF and LMW-DS or G-CSF and AMD3100 compared to CAM buffer (vehicle). Blood was sampled after 30 minutes (LMW-DS and vehicle) or 1 hour (AMD3100). Mean±SEM is shown. Statistical analysis compared G-CSF+LMW-DS or G-CSF and AMD3100 to control group (G-CSF+CAM) (*$p<0.05$, $p<0.01$, *$p<0.001$) or G-CSF+LMW-DS compared to G-CSF+AMD3100 ($^{554}p<0.05$, $^{††}p<0.01$, $^{†††}p<0.001$).

G-CSF increased the number of WBC compared to normal (see FIGS. 1 and 3 for CAM administration only) and addition of dextran sulfate (25 and 100 mg/kg) increased the WBC and lymphocyte number in a synergistic mode. The increase of WBC and lymphocytes was significantly more pronounced than after AMD3100 (5 mg/kg) administration (FIG. 6).

Figure 7A:
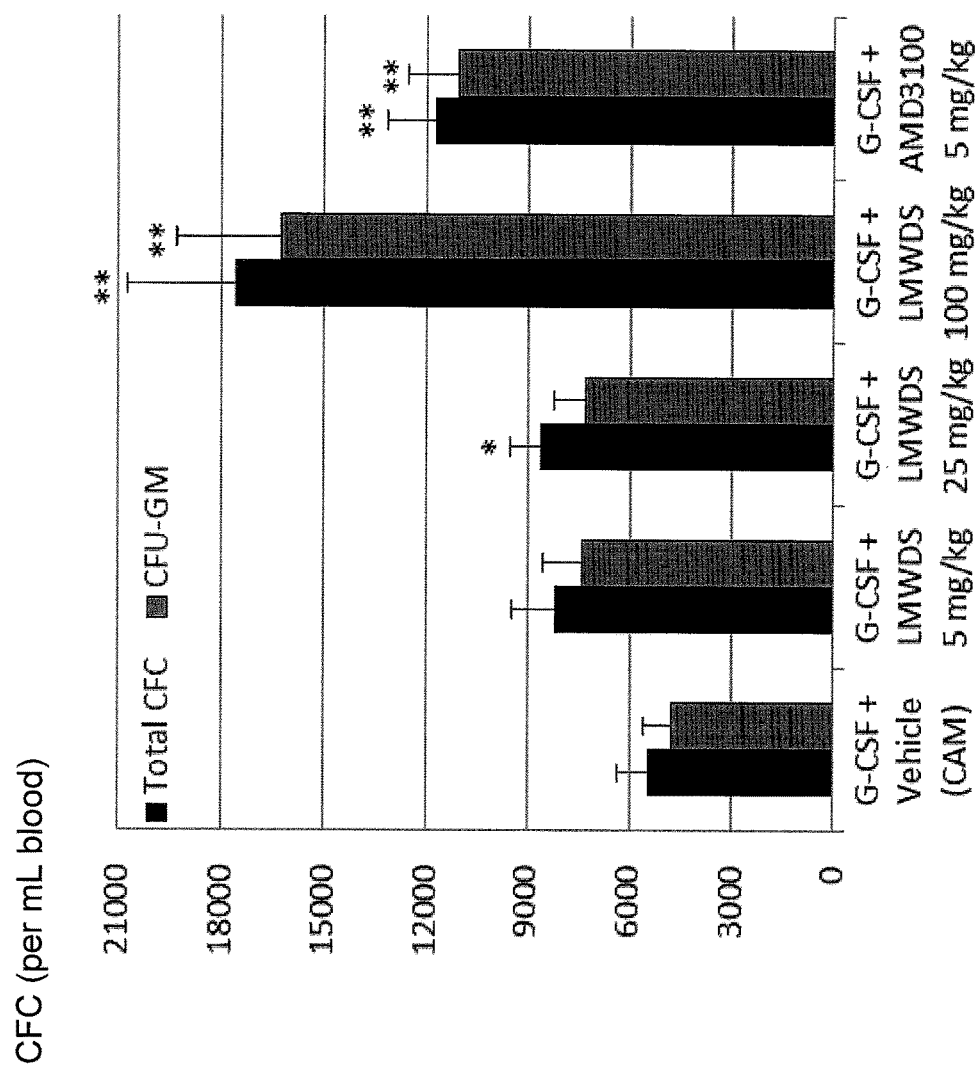
FIGS. 7A and 7B illustrate combination treatment of G-CSF and LMW-DS or G-CSF and AMD3100 in mobilization of progenitor cells in peripheral blood. CAM buffer was used as vehicle control. Blood was sampled after 30 minutes (LMW-DS and vehicle) or 1 hour (AMD3100). Mean±SEM is shown. Statistical analysis compared G-CSF+LMW-DS or G-CSF and AMD3100 to control group (G-CSF+CAM) (*$p<0.05$, **$p<0.01$) or G-CSF+LMW-DS compared to G-CSF+AMD3100 ($^{554}$ $p<0.05$, $^{††}p<0.01$).
Figure 7B:
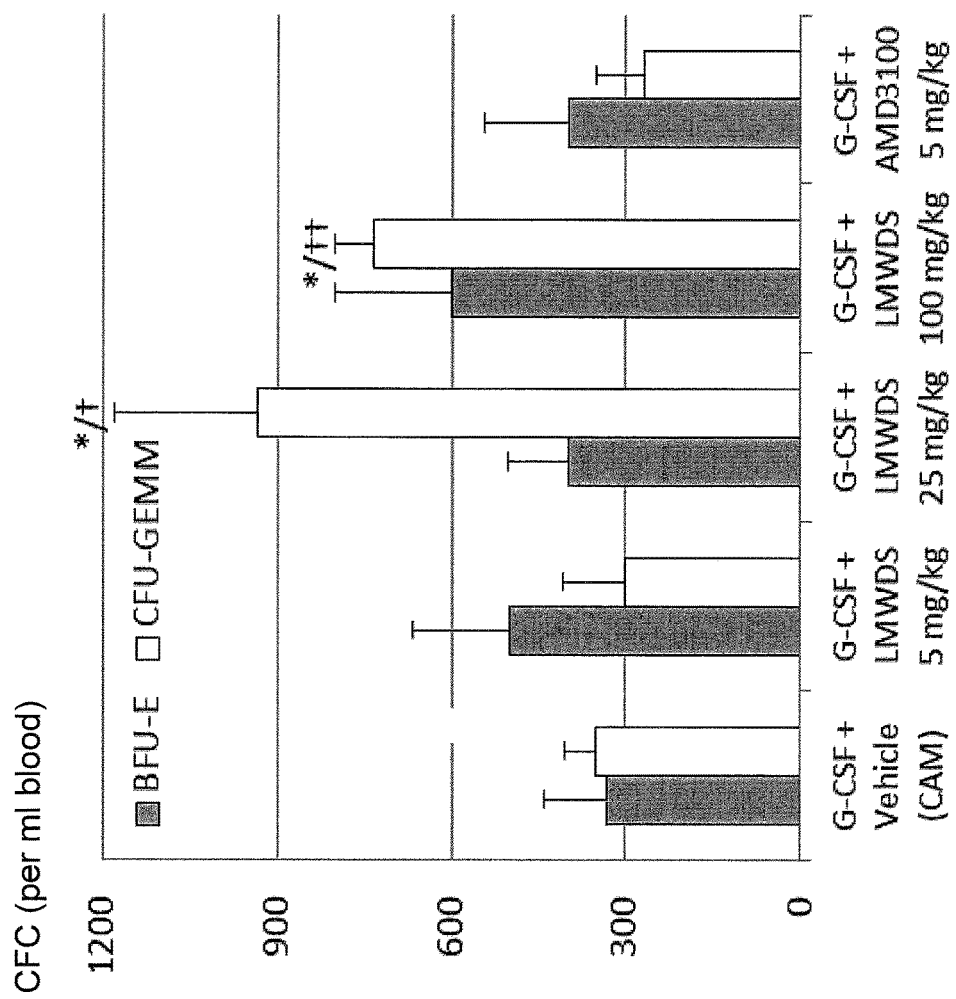
Figure 8:
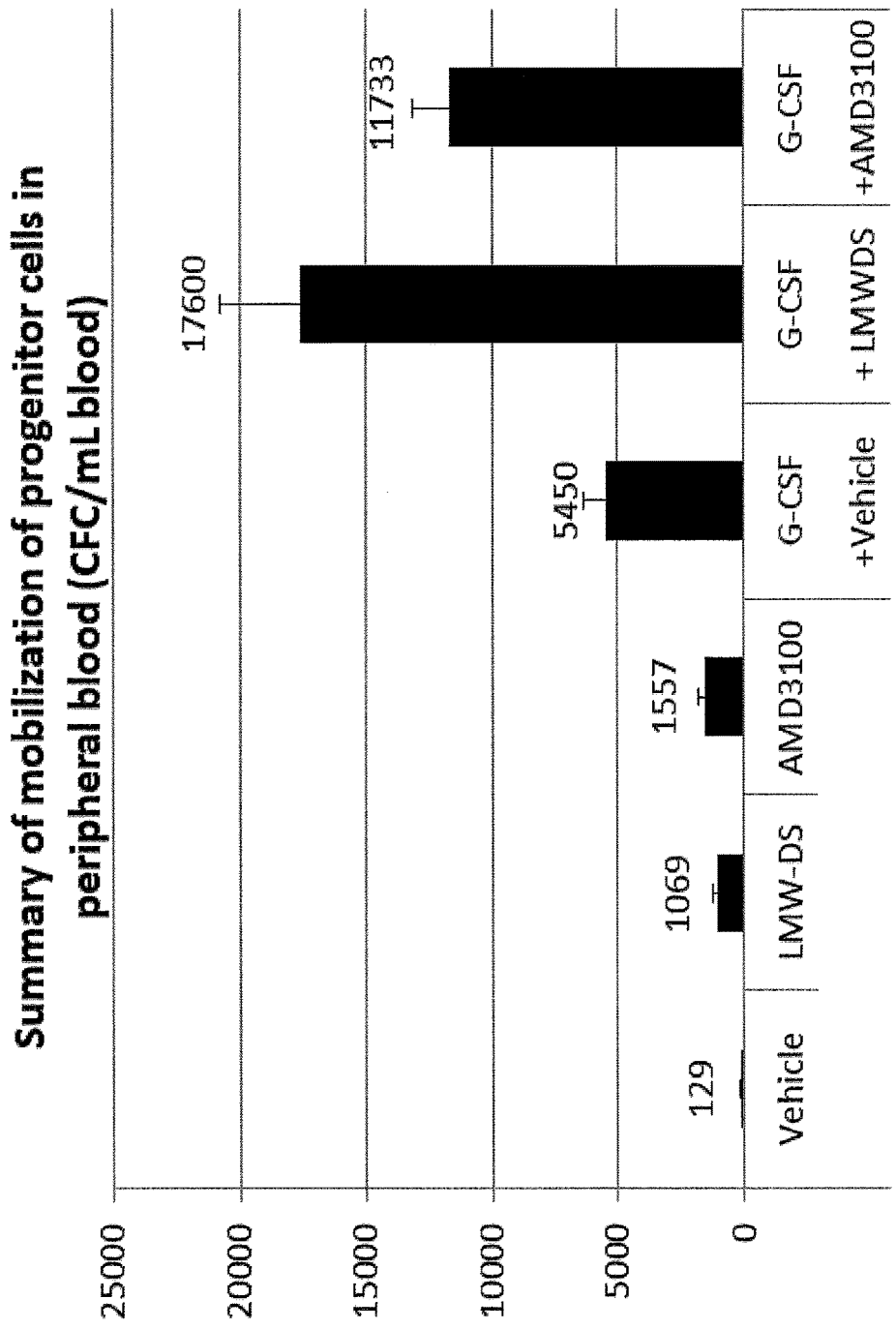
FIG. 8 is an overview of mobilization of progenitor cells after single injections in mice of 100 mg/kg LMW-DS, G-CSF, G-CSF+LMW-DS, G-CSF+AMD3100 (5 mg/kg) or CAM (vehicle). Combinatory treatment with G-CSF and LMW-DS significantly increased the number of CFC compared to CAM buffer, LMW-DS, and G-CSF. Error bars show SEM, n=6-10.
Figure 9:
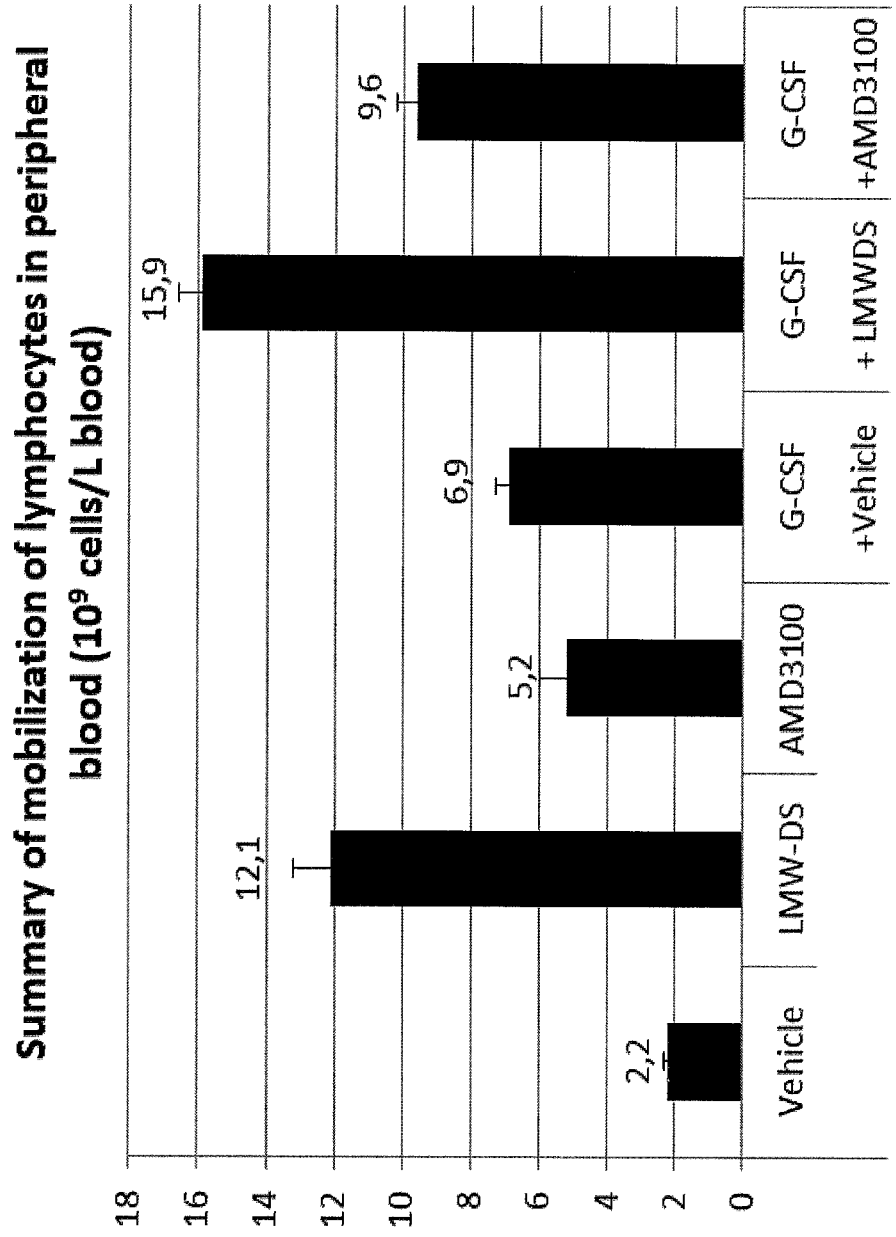
FIG. 9 is an overview of mobilization of lymphocytes after single injections in mice of 100 mg/kg LMW-DS, G-CSF, G-CSF+LMW-DS, G-CSF+AMD3100 (5 mg/kg) or CAM (vehicle). LMW-DS administration increased lymphocytes in peripheral blood compared to single therapy of G-CSF or AMD3100 and in combination with G-CSF the increase was significant compared to G-CSF+AMD3100. Error bars show SEM, n=6-10.

Addition of dextran sulfate in a dose of 100 mg/kg to G-CSF renders a vast and synergistic increase of progenitor cells in peripheral blood and dextran sulfate seemed to be more efficient as a mobilizing agent than AMD3100 (FIGS. 7A and 7B). The combination of dextran sulfate and G-CSF mobilized more CFU-GEMM and BFU-E progenitors (FIG. 7B) compared to the G-CSF and AMD3100 combination.

The conducted experiments showed a dose-effect relationship of dextran sulfate on mobilization of WBC, lymphocytes, and CFC both after s.c. and i.v. administration. The increase of CFC seemed to be higher (6-12 times over control) compared to the general increase of WBC (4-5 times over control). The time effect of i.v. administered dextran sulfate (100 mg/kg) was a rapid increase in CFC, WBC, and lymphocytes. The peak started already after 7.5 minutes, which was significantly earlier than for AMD3100. The combination of dextran sulfate with G-CSF showed an unexpected and pronounced increase of CFC in peripheral blood to up to 18000 CFC (more than 100-fold over control), and seemingly more efficient compared to AMD3100 in combination with G-CSF, see FIG. 8. Dextran sulfate administration resulted in a significantly higher mobilization of WBC and lymphocytes, and seemed also to mobilize more BFU-E in mono-therapy versus an optimal dose of AMD3100. Dextran sulfate administration in combination with G-CSF resulted in a significantly higher mobilization of WBC and lymphocytes, and seemed also to mobilize more CFC, BFU-E, and CFU-GEMM versus AMD3100, see FIGS. 7A, 7B, 8 and 9. Dextran sulfate increased the HGF in plasma to high levels (from <160 to 16000 pg/mL) 15 minutes after administration, 25-fold more than AMD3100 after 1 hour.

Comparison on Mobilization of Hematopoietic Cells by Low Molecular Weight Dextran Sulfate of Different Average Molecular Weights Animals Female DBA/2Ola mice (Harlan, Holland) were kept at the animal facility at Uppsala University housed under standard conditions and were provided with food and water ad libitum. Animals weighing 17-22 g were used.

Experimental Design

DBA/2-females were grouped into four groups: 1) vehicle (aq. NaCl) (n=8), 2) 50 mg/kg dextran sulfate DS3 (n=5), 3) 50 mg/kg dextran sulfate DS5 (n=5) and 4) 50 mg/kg dextran sulfate DS5 PNB (n=5). Group 4) was sedated with sodium pentobarbital (PNB) instead of isoflurane, to evaluate if a change in anesthesia protocol affects mobilization.

Administration of Substance

DS5 (average Mw 5.1 kDa, pKC Denmark, batch 31497) and DS3 (average Mw 3.3 kDa, TdB Consultancy, Uppsala Sweden, batch 20341) were dissolved in 0.9% NaCl (Fresenius Kabi), to 20 mg/mL and filtered through 20 µm filter to obtain a sterile solution. The animals received 2.5 mL/kg (app. 50 µL) intravenously through the tail vein.

Hematological Analysis

The results are shown in FIG. 10 and Table 6. DS3 did not show any significant alteration in overall WBC or lymphocytes whereas a slight decrease in neutrophils was reported.

TABLE 6 hematological variables in peripheral blood after administration of dextran sulfate substances

| | Unit | Vehicle | DS3 | DS5 | DS5 PNB |
|---|---|---|---|---|---|
| Platelets | $10^9$/L | 943 ± 40 | 925 ± 30 | 950 ± 31 | 980 ± 11 |
| Hemoglobin | g/L | 128 ± 2 | 128 ± 4 | 129 ± 3 | 135 ± 2* |
| Erythrocytes | $10^{12}$/L | 10 ± 0.1 | 9.6 ± 0.2 | 9.7 ± 0.2 | 10.1 ± 0.2* |
| Hematocrit (EFV) | | 0.42 ± 0.005 | 0.42 ± 0.008 | 0.43 ± 0.008 | 0.44 ± 0.01* |

TABLE 6-continued hematological variables in peripheral blood after administration of dextran sulfate substances

|  | Unit | Vehicle | DS3 | DS5 | DS5 PNB |
|---|---|---|---|---|---|
| MCV | fL | 44 ± 0.3 | 44 ± 0 | 44 ± 0.4 | 44 ± 0.3 |
| MCHC | g/L | 308 ± 1 | 302 ± 6 | 305 ± 1 | 304 ± 4 |
| Reticulocytes | $10^9$/L | 3 ± 0.4 | 3 ± 0.4 | 4 ± 0.6 | 4 ± 0.4 |
| Leukocytes (WBC) | $10^9$/L | 3 ± 0.2 | 3.0 ± 0.4 | 10.1 ± 1.0*** | 8.5 ± 0.7*** |
| Neutrophils | $10^9$/L | 1.0 ± 0.1 | 0.7 ± 0.1* | 1.4 ± 0.2* | 0.8 ± 0.2 |
| Eosinophils | $10^9$/L | 0.1 ± 0.02 | 0.1 ± 0 | 0.1 ± 0 | 0.1 ± 0 |
| Basophils | $10^9$/L | 0.1 ± 0 | 0.1 ± 0 | 0.1 ± 0 | 0.1 ± 0 |
| Lymphocytes | $10^9$/L | 2 ± 0.1 | 2.2 ± 0.4 | 8.5 ± 0.9*** | 7.4 ± 0.7*** |
| Monocytes | $10^9$/L | 0.05 ± 0.02 | 0.02 ± 0.02 | 0.1 ± 0 | 0.06 ± 0.02 |
| Time of blood sample after DS | min | 31 ± 0.3 | 32 ± 0.4 | 31 ± 0.2 | 33 ± 1.4 |

MVC = Mean Corpuscular Volume;
MCHC = Mean Corpuscular Hemoglobin Concentration
Hematological variables compared to vehicle (NaCl):
*p < 0.05,
**p < 0.01.
***p < 0.001

DS3 did not induce a significant increase in the number of CFC, as shown in FIG. 11. DS5 induced a significant increase in HGF independent of the use of anesthesia, whereas the lower molecular weight substance (DS3) showed no significant increase in HGF, see FIG. 12. The data presented herein shows that DS3 is a poor mobilizing agent compared to DS5. DS3 does not increase HGF to any degree beyond vehicle.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

Broxmeyer et al. (1999) "Dominant myelopoietic effector functions mediated by chemokine receptor CCR1" J Exp Med 189(12): 1987-92

Broxmeyer et al. (2005) "Rapid mobilization of murine and human hematopoietic stem and progenitor cells with AMD3100, a CXCR4 antagonist" J Exp Med 201(8): 1307-18

Chemaly et al. (2006) "Respiratory viral Infections in adults with hematologic malignancies and human stem cell transplantation recipients" Medicine 85(5): 278-287

CHMP Assessment Report Mozobil (plerixafor) Procedure No. EMEA/H/C/001030, 2009

Cooper et al. (1997) "Erythroid burst-forming units (BU-E) predict hematopietic recovery after peripheral blood progenitor cell transplantation in patients with advanced breast cancer" Bone Marrow Transplantation 19: 1089-94

Copelan (2006) "Hematopoietic Stem-cell Transplantation" N Engl J Med 354: 1813-26

Galimi et al. (1994) "Hepatocyte growth factor induces proliferation and differentiation of multipotent and erythroid hematopoietic progenitors" J Cell Biol 127(6 Pt 1): 1743-54

Goff et al. (1996) "Synergistic effects of hepatocyte growth factor on human cord blood CD34+ progenitor cells are the result of c-met receptor expression" Stem Cells 14(5): 592-602

Han et al. (1998) "Effect of combination of DS and G-CSF on mobilization of peripheral hematopoietic progenitors in mice" Journal of Experimental Hematology 6: 29-31

Hassan et al. (1997) "Factors influencing hematological recovery after allogeneic bone marrow transplantation in leukaemia patients treated with methotrexate-containing GVHD prophylaxis" Support Care Cancer 5: 299-306

Hayakawa et al. (2009) "Dextran sulfate and stromal cell derived factor-1 promote CXCR4 expression and improve bone marrow homing efficiency of infused hematopoietic stem cells" J Nippon Med Sch 76(4): 198

Hiwase et al. (2008) "Higher infused lymphocyte dose predicts higher lymphocyte recovery, which in turn, predicts superior overall survival following autologous hematopoietic stem cell transplantation for multiple myeloma" Biol Blood & Marrow Transpl 14: 116-24

Kalatskaya et al. (2009) "AMD3100 is a CXCR7 ligand with allosteric agonist properties" Mol Pharmacol 75(5): 1240-7

Kmiecik et al, (1992) "Hepatocyte growth factor is a synergistic factor for the growth of hematopoietic progenitor cells" Blood 80(10): 2454-7

Lapidot et al. (2003) "Current understanding of factors influencing stem cell mobilization" Hematology (Am Soc Hematol Educ Program), 419-37

Mozobil™ Product Monograph, moZoBil™ (plerixafor injection), genzyme

Pablos et al. (2003) "Synoviocyte-derived CXCL 12 is displayed on endothelium and induces angiogenesis in rheumatoid arthritis" J Immunol 170: 2147-52

Porrata et al. (2004a) "Infused peripheral blood autograft absolute lymphocyte count correlates with day 15 absolute lymphocyte count and clinical outcome after autologous peripheral hematopoietic stem cell transplantation in non-Hodgkin's lymphoma" Bone Marrow Transpl 33: 291-8

Porrata et al. (2004b) "The dose of infused lymphocytes in the autograft directly correlates with clinical outcome after autologous peripheral blood hematopoietic stem cell transplantation in multiple myeloma" Leukemia 18: 1085-92

Porrata (2009) "Clinical Evidence of Autologous Graft versus Tumor Effect" Am J Immunol 5(1): 1-7

Roodman et al. (1987) "CFU-GEMM correlate with neutrophil and platelet recovery in patients receiving autologous marrow transplantation after high-dose melphalan chemotherapy" Bone Marrow Transpl 2: 195-73

Roos et al. (1995) "Induction of liver growth in normal mice by infusion of hepatocyte growth factor/scatter factor" Am J Physiol 268(2 Pt 1): 380-6

Sweeney et al. (2000) "Mobilization of stem/progenitor cells by sulfated polysaccharides does not require selectin presence" PNAS 97(12): 6544-49

Sweeney et al. (2002) "Sulfated polysaccharides increase plasma levels of SDF-1 in monkeys and mice: involvement in mobilization of stem/progenitor cells" Blood 99(1): 44-51

Weimar et al. (1998) "Hepatocyte growth factor/scatter factor (HGF/SF) is produced by human bone marrow stromal cells and promotes proliferation, adhesion and survival of human hematopoietic progenitor cells (CD34+)" Exp Hematol 26(9): 885-94

Yu et al. (1998) "Stimulatory effects of hepatocyte growth factor on hemopoiesis of SCF/c-kit system-deficient mice" Stem cells 16(1): 66-77

Zioncheck et al. (1995) "Sulfated oligosaccharides promote hepatocyte growth factor association and govern its mitogenic activity" J Biol Chem 270(28): 16871-8

The invention claimed is:

1. A method of mobilizing progenitor cells having an ability to form colony forming units (CFUs) and/or CD34$^+$ stem cells into the peripheral blood of a human subject, said method comprising administering to the human subject dextran sulfate having an average molecular weight in a range of 3500 to 7000 Da, or a pharmaceutically acceptable derivative thereof, in an amount effective to mobilize the progenitor cells and/or CD34+stem cells into the peripheral blood of the human subject; and within a time period of 0.5 to 4 hours after administration of the dextran sulfate, begin harvesting said progenitor cells and/or CD34$^+$stem cells from the peripheral blood of the human subject.

2. The method according to claim 1, wherein said progenitor cells are colony forming cells selected from a group consisting of colony forming unit—granulocyte, erythrocyte, monocyte, megakaryocyte (CFU-GEMM), and burst forming unit-erythrocyte (BFU-E).

3. The method according to claim 1, wherein said dextran sulfate, or said pharmaceutically acceptable derivative thereof, has an average molecular weight in a range of 4500 to 7000 Da.

4. The method according to claim 3, wherein said dextran sulfate, or said pharmaceutically acceptable derivative thereof, has an average molecular weight in a range of 4500 to 5500 Da.

5. The method according to claim 1, wherein said dextran sulfate, or said pharmaceutically acceptable derivative thereof, has an average sulfur content in a range from 15 to 20%.

6. The method according to claim 5, wherein said dextran sulfate, or said pharmaceutically acceptable derivative thereof, has an average sulfur content of about 17%.

7. The method according to claim 1, wherein said dextran sulfate, or said pharmaceutically acceptable derivative thereof, is formulated as an aqueous injection solution.

8. The method according to claim 1, wherein said dextran sulfate, or said pharmaceutically acceptable derivative thereof, is administered at a dosage in a range from 0.1 to 50 mg/kg of body weight of said subject.

9. The method according to claim 8, wherein said dextran sulfate, or said pharmaceutically acceptable derivative thereof, is administered at a dosage in a range from 1 to 50 mg/kg of body weight of said subject.

10. The method according to claim 9, wherein said dextran sulfate, or said pharmaceutically acceptable derivative thereof, is administered at a dosage in a range from 5 to 25 mg/kg body weight of said subject.

11. The method according to claim 1, wherein G-CSF is administered to said subject once or twice 2-4 days prior to the time point at which harvesting of said progenitor cells and/or CD34$^+$stem cells from said peripheral blood of said subject is begun, in an amount effective to increase mobilized progenitor cells and/or CD34+ stem cells into the peripheral blood of the subject.

12. The method according to claim 11, wherein said effective amount of G-CSF is administered to said subject additionally on a day of said time point at which harvesting of said progenitor cells and/or CD34$^+$stem cells from said peripheral blood of said subject is begun.

13. The method according to claim 12, wherein the G-CSF and the dextran sulfate are administered separately to the subject.

14. The method according to claim 1, wherein said dextran sulfate, or said pharmaceutically acceptable derivative thereof further induces hepatocyte growth factor (HGF) into said blood stream of said subject.

15. The method according to claim 1, wherein harvesting said progenitor cells and/or CD34+ stem cells from the peripheral blood of the human subject is begun within a time period of 0.5 to 3 hours after administration of the dextran sulfate.

16. The method according to claim 1, wherein the harvesting is conducted for not more than 4 hours.

17. The method according to claim 1, wherein G-CSF is administered to said subject simultaneously with the administration of the dextran sulfate.

\* \* \* \* \*

UNITED STATES PATENT AND TRADEMARK OFFICE
CERTIFICATE OF CORRECTION

PATENT NO. : 10,258,642 B2
APPLICATION NO. : 14/890636
DATED : April 16, 2019
INVENTOR(S) : Anders Waas et al.

It is certified that error appears in the above-identified patent and that said Letters Patent is hereby corrected as shown below:

On the Title Page

Item (30), change "1350584" to --1350584-7--.

Signed and Sealed this
Fourth Day of June, 2019

Andrei Iancu
*Director of the United States Patent and Trademark Office*